US009000229B2

(12) United States Patent
Devon et al.

(10) Patent No.: US 9,000,229 B2
(45) Date of Patent: Apr. 7, 2015

(54) PRODUCTION OF HYDROXY ETHER HYDROCARBONS BY VAPOR PHASE HYDROGENOLYSIS OF CYCLIC ACETALS AND KETALS

(75) Inventors: Thomas James Devon, Longview, TX (US); Damon Ray Billodeaux, Longview, TX (US)

(73) Assignee: Eastman Chemical Company, Kingsport, TN (US)

(*) Notice: Subject to any disclaimer, the term of this patent is extended or adjusted under 35 U.S.C. 154(b) by 512 days.

(21) Appl. No.: 13/168,274

(22) Filed: Jun. 24, 2011

(65) Prior Publication Data
US 2012/0330066 A1 Dec. 27, 2012

(51) Int. Cl.
C07C 41/14 (2006.01)
C07C 41/28 (2006.01)

(52) U.S. Cl.
CPC .................................... C07C 41/28 (2013.01)

(58) Field of Classification Search
USPC ......................................................... 568/678
See application file for complete search history.

(56) References Cited

U.S. PATENT DOCUMENTS

| | | | |
|---|---|---|---|
| 2,425,042 A | 8/1947 | McNamee et al. | |
| 2,429,878 A | 10/1947 | Gresham et al. | |
| 2,486,024 A * | 10/1949 | Hearne et al. ................. | 568/679 |
| 3,275,680 A | 9/1966 | Holzrichter et al. | |
| 4,024,159 A | 5/1977 | Peterson | |
| 4,038,175 A | 7/1977 | Bhasin | |
| 4,062,898 A | 12/1977 | Dubeck et al. | |
| 4,071,568 A | 1/1978 | Onoda et al. | |
| 4,088,700 A | 5/1978 | Watts | |
| 4,169,959 A | 10/1979 | Arpe | |
| 4,308,403 A | 12/1981 | Knifton | |
| 4,317,943 A | 3/1982 | Knifton | |
| 4,356,327 A | 10/1982 | Knifton | |
| 4,357,477 A | 11/1982 | Knifton | |
| 4,375,394 A | 3/1983 | Devon | |
| 4,390,734 A | 6/1983 | Knifton | |
| 4,430,253 A | 2/1984 | Dubeck | |
| 4,435,595 A | 3/1984 | Agreda et al. | |
| 4,478,017 A | 10/1984 | Brown et al. | |
| 4,479,017 A | 10/1984 | Ayusawa et al. | |
| 4,482,753 A | 11/1984 | Tai-Huang et al. | |
| 4,484,009 A | 11/1984 | Ghenassia et al. | |
| 4,537,980 A | 8/1985 | Greenshields | |
| 4,568,780 A | 2/1986 | Knifton | |
| 4,617,287 A | 10/1986 | Lyons | |
| 4,618,729 A | 10/1986 | Duggan et al. | |
| 4,663,489 A | 5/1987 | Duggan et al. | |
| 4,692,426 A | 9/1987 | Duggan et al. | |
| 4,847,425 A | 7/1989 | Degner et al. | |
| 4,895,818 A | 1/1990 | Duggan et al. | |
| 4,895,987 A | 1/1990 | Duggan et al. | |
| 4,939,294 A | 7/1990 | Agreda et al. | |
| 5,319,148 A | 6/1994 | Karcher et al. | |
| 5,362,918 A | 11/1994 | Aizawa et al. | |
| 5,399,631 A | 3/1995 | Egawa et al. | |
| 5,446,208 A | 8/1995 | Koshino et al. | |
| 5,446,210 A | 8/1995 | Hees et al. | |
| 5,523,491 A | 6/1996 | Egawa et al. | |
| 5,589,597 A | 12/1996 | Egawa et al. | |
| 5,616,736 A | 4/1997 | Thigpen | |
| 5,720,895 A | 2/1998 | Nakagawa et al. | |
| 5,763,691 A | 6/1998 | Kawabe | |
| 5,780,687 A | 7/1998 | Holderich et al. | |
| 5,821,391 A * | 10/1998 | Holderich et al. ............ | 568/678 |
| 5,866,735 A | 2/1999 | Cheung | |
| 5,886,198 A | 3/1999 | Ogawa et al. | |
| 5,917,059 A | 6/1999 | Bruchmann et al. | |
| 5,935,896 A | 8/1999 | Dupuis et al. | |
| 6,013,844 A | 1/2000 | Heineke et al. | |
| 6,015,875 A | 1/2000 | Smith et al. | |
| 6,028,215 A | 2/2000 | Bessling et al. | |
| 6,080,897 A | 6/2000 | Kawabe | |
| 6,087,539 A | 7/2000 | Yamasaki et al. | |
| 6,124,479 A | 9/2000 | Hinoue et al. | |
| 6,136,576 A | 10/2000 | Diaz-Torres | |
| 6,143,908 A | 11/2000 | Hinoue et al. | |
| 6,166,240 A | 12/2000 | Jiang et al. | |
| 6,207,850 B1 | 3/2001 | Jiang et al. | |
| 6,232,512 B1 | 5/2001 | Haas et al. | |
| 6,265,623 B1 | 7/2001 | Morawietz et al. | |
| 6,291,725 B1 | 9/2001 | Chopade | |

(Continued)

FOREIGN PATENT DOCUMENTS

| | | |
|---|---|---|
| CA | 1 254 190 | 5/1989 |
| DE | 419223 C | 9/1925 |

(Continued)

OTHER PUBLICATIONS

Coelho, Antonio Carlos Vieira, et al.; "Surface Area, Crystal Morphology and Characterization of Transition Alumina Powders from a New Gibbsite Precursor"; Materials Research, vol. 10, No. 2, pp. 183-189, (2007), XP002683656.

Hudson, L. Keith, et al.; "Aluminum Oxide", Internet Citation XP-002596245, pp. 1-40, Jun. 15, 2000, URL: http://onlinelibrary.wiley.com/doi/10.

Hibbert, H., et al.: Studies on the reactions relating to carbohydrates and polysaccharides. X. Synthesis and relative stability of cyclic acetals from 1, 2- and 1, 3-glycols; Journal of the American Chemistry Society, vol. 46, No. 5, 1924. pp. 1283-1290, XP002621973, cited in the application pp. 1286, 1287, "Experimental Part".

Notification of Transmittal of the International Search Report and the Written Opinion of the International Searching Authority dated Jun. 19, 2012 for International Application No. PCT/US2012/043085.

(Continued)

Primary Examiner — Rosalynd Keys
(74) Attorney, Agent, or Firm — Dennis V. Carmen

(57) ABSTRACT

A vapor phase hydrogenolysis reaction to convert cyclic acetal compounds and/or cyclic ketal compounds in the presence of hydrogen to their corresponding hydroxy ether hydrocarbon reaction products using a supported noble metal catalyst. The hydrogenolysis reaction can be carried out in the vapor phase and in the absence of a polyhydroxyl hydrocarbon co-solvent.

48 Claims, No Drawings

(56) References Cited

U.S. PATENT DOCUMENTS

| | | | |
|---|---|---|---|
| 6,380,419 | B2 | 4/2002 | Kawabe |
| 6,458,992 | B1 | 10/2002 | Lederer et al. |
| 6,518,464 | B2 | 2/2003 | Therre et al. |
| 6,548,681 | B1 | 4/2003 | Chopade et al. |
| 6,657,089 | B1 | 12/2003 | Nagasawa et al. |
| 6,670,489 | B2 | 12/2003 | Koyama et al. |
| 6,713,640 | B2 | 3/2004 | Miller et al. |
| 6,969,779 | B2 | 11/2005 | Brewer et al. |
| 7,030,277 | B2 | 4/2006 | Groten et al. |
| 7,060,372 | B2 | 6/2006 | Fryd et al. |
| 7,071,362 | B2 | 7/2006 | Sugawara et al. |
| 7,160,524 | B2 | 1/2007 | Lederer et al. |
| 7,301,055 | B2 | 11/2007 | Hoffmockel et al. |
| 7,321,052 | B2 | 1/2008 | Miller et al. |
| 7,488,851 | B2 | 2/2009 | Egidio Rodrigues et al. |
| 7,498,451 | B2 | 3/2009 | Haderlein et al. |
| 7,534,922 | B2 | 5/2009 | Gorling et al. |
| 7,754,900 | B2 | 7/2010 | Siegert et al. |
| 2006/0129000 | A1 | 6/2006 | Goring et al. |
| 2008/0283384 | A1 | 11/2008 | Lang et al. |
| 2010/0048940 | A1 | 2/2010 | Tulchinsky et al. |
| 2010/0099894 | A1 | 4/2010 | Dubois et al. |
| 2010/0158780 | A1 | 6/2010 | Galligan et al. |
| 2010/0228065 | A1 | 9/2010 | Cheung et al. |
| 2010/0261936 | A1 | 10/2010 | Okumura et al. |
| 2010/0292491 | A1 | 11/2010 | Selifonov et al. |
| 2011/0034739 | A1 | 2/2011 | Stochniol et al. |
| 2011/0207969 | A1 | 8/2011 | Olken et al. |

FOREIGN PATENT DOCUMENTS

| | | | |
|---|---|---|---|
| DE | 3328561 | A1 | 2/1985 |
| DE | 238 232 | A1 | 8/1986 |
| DE | 19648960 | A1 | 5/1998 |
| DE | 10036423 | A1 | 3/2001 |
| EP | 0 168 989 | A1 | 1/1986 |
| EP | 0 169 666 | B1 | 1/1986 |
| EP | 0 271 091 | A1 | 6/1988 |
| EP | 0 312 659 | A1 | 4/1989 |
| EP | 0499055 | A2 | 8/1992 |
| EP | 0616994 | A2 | 9/1994 |
| EP | 0 624 563 | A1 | 11/1994 |
| EP | 0696564 | A1 | 2/1996 |
| EP | 1 236 511 | A1 | 9/2002 |
| FR | 2 906 246 | A1 | 3/2008 |
| GB | 1020500 | A | 2/1966 |
| JP | 52073810 | A | 6/1977 |
| JP | 56166186 | A | 12/1981 |
| JP | 58198431 | A | 11/1983 |
| JP | 5155878 | A | 6/1993 |
| JP | 5271217 | A | 10/1993 |
| JP | 6128184 | A | 5/1994 |
| JP | 2001072636 | A | 3/2001 |
| JP | 4287546 | B2 | 7/2009 |
| WO | WO 01/19763 | A1 | 3/2001 |
| WO | WO 03/002547 | A1 | 1/2003 |
| WO | WO 2010/027663 | A1 | 3/2010 |

OTHER PUBLICATIONS

Notification of Transmittal of the International Search Report and the Written Opinion of the International Searching Authority dated Jun. 14, 2012 for International Application No. PCT/US2012/042378.
Notification of Transmittal of the International Search Report and the Written Opinion of the International Searching Authority dated Jun. 8, 2012 for International Application No. PCT/US2012/041459.
Notification of Transmittal of the International Search Report and the Written Opinion of the International Searching Authority dated Sep. 3, 2012 for International Application No. PCT/US2012/042458.
Notification of Transmittal of the International Search Report and the Written Opinion of the International Searching Authority dated Sep. 11, 2012 for International Application No. PCT/US2012/043071.
Notification of Transmittal of the International Search Report and the Written Opinion of the International Searching Authority dated Oct. 15, 2012 for International Application No. PCT/US2012/042453.
Notification of Transmittal of the International Search Report and the Written Opinion of the International Searching Authority dated Sep. 14, 2012 for International Application No. PCT/US2012/043093.
USPTO Office Action dated Nov. 9, 2012 for co-pending U.S. Appl. No. 13/168,374.
USPTO Office Action dated Nov. 26, 2012 for co-pending U.S. Appl. No. 13/168,229.
Knifton "Syngas reactions: Part VIII: The preparation of glycol monoalkyl ethers," Journal of Molecular Catalysis 1985, 30, pp. 281-297.
Jakab et al. "Synthesis, regioselective hydrogenolysis, partial hydrogenation, and conformational study of dioxane and dkoxane-type (9-anthracenyl)methylene acetals of sugars," Carbohydrate Research 2009, 344, pp. 2444-2453.
Broekhuis et al. "Recovery of Propylene Glycol from Dilute Aqueous Solutions via Reversible Reaction with Aldehydes" Ind. Eng. Chem. Res. 1994, 33, pp. 3230-3237.
Dhale et al. "Propylene Glycol and Ethylene Glycol Recovery from Aqueous Solution via Reactive Distillation" Chemical Engineering Science, 2004, 59, pp. 2881-2890.
Hao et al. "Downstream processing of 1,3-propanediol fermentation broth" J. Chem. Technol. Biotechnol. 2006, 81, pp. 102-108.
Howard et al. "Hydrogenolysis of Ketals" J. Org. Chem., 1961 26(4), pp. 1026-1028.
Osman et al. "Cyclic Acetal Formation Between 2-Pyridinecarboxaldehyde and y-Hydroxy-a,b-Acetylenic Esters" Tetrahedron Lett. 2008, 49 (46) pp. 6550-6552.
Zajac et al. "Reaction of 2-Butynal Diethyl Acetal with Lithium Aluminum Hydride" J. Org. Chem., 1975 40(4), pp. 530-531.
Astle et al. "Catalysis with Cation-Exchange Resins, Preparation of 1,3 Dioxolanes and 1,3,6-Trioxocanes", Industrial and Engineering Chemistry, Apr. 1954, pp. 787-791.
Singh et al. "Production of Butyl Acetate by Catalytic Distillation. Theoretical and Experimental Studies" Ind. Eng. Chem. Res. 2005, 44, pp. 3042-3052.
Venimadhavan et al. "A Novel Distillate Policy for Batch Reactive Distillation with Application to the Production of Butyl Acetate" Ind. Eng. Chem. Res. 1999, 38, pp. 714-722.
Chadda et al. "Feasibility and Synthesis of Hybrid Reactive Distillation Systems" AIChE Journal, Dec. 2002, vol. 48, No. 12, pp. 2754-2768.
Hibbert et al., J. Am. Chem. Soc. 1924, 46(5), pp. 1283-1290.
Sulzbacher et al., J. Am. Chem. Soc. 1948, 70(8), pp. 2827-2828.
Bronsted and Grove, J. Am. Chem. Soc. 1930, 52(4), pp. 1394-1403.
Van Duzee et al., J. Am. Chem. Soc. 1935, 57, p. 147.
Bonner et al., J. Am. Chem. Soc., Perkins Trans. 1981, pp. 1807-1810.
Tkachenko et al. "Research in the Field of Furan Acetal Compounds. XII. Features of the Vapor-Phase Hydrogenation of Disubstituted 1,3-Dioxolanes", Chemistry and Technology of Furan Compounds, 1985, pp. 59-64.
Public Dow literature, "Dow Technology Licensing—METEOR™ Ethylene Oxide/Glycol Process Technology," http://www.dow.com/licensing/offer/meteor.htm (downloaded and printed from the internet on Aug. 24, 2011).
Public Shell literature, "Factsheets: OMEGA and ethylene oxide/ethylene glycol technology," http://www.shell.com/home/content/chemicals/ aboutshell/media_centre/factsheets/omega/ (downloaded and printed from the internet on Aug. 24, 2011).
Public website at http://globalbiochemna.com/, Global BioChem Technology Group (GBT), Product Information, "About Us, and Glycols Project/Polyol Chemicals" (downloaded and printed from the internet on Aug. 24, 2011).
Public Dow literature, Dow Product Safety Assessment, "Ethylene Glycol Butyl Ether" (EGBE), at http://www.dow.com/productsafety, Product Safety Assessment Finder. (downloaded and printed from the internet on Aug. 24, 2011).
Kul'nevich et al., Khimiya Geterotsiklicheskikh Soyedinenii, No. 8, 1977, pp. 1026-1029.
U.S. Appl. No. 13/168,229, filed Jun. 24, 2011.

(56) References Cited

OTHER PUBLICATIONS

U.S. Appl. No. 13/168,304, filed Jun. 24, 2011.
U.S. Appl. No. 13/168,330, filed Jun. 24, 2011.
U.S. Appl. No. 13/168,349, filed Jun. 24, 2011.
U.S. Appl. No. 13/168,361, filed Jun. 24, 2011.
U.S. Appl. No. 13/168,374, filed Jun. 24, 2011.
Luyben, William L., et al.; "Reactive Distillation Design and Control", John Wiley & Songs, 2008, p. 514-517.
Stichlmair, Johann, et al.; "Reactive Distillation Processes"; Chemical Engineering Technology, 22 (1999) 2; pp. 95-103.
USPTO Office Action dated May 21, 2013 for co-pending U.S. Appl. No. 13/168,374.
USPTO Office Action dated Jul. 1, 2013 for co-pending U.S. Appl. No. 13/168,229.
USPTO Office Action dated Aug. 15, 2013 for copending U.S. Appl. No. 13/168,330.
USPTO Office Action dated Nov. 1, 2013 for copending U.S. Appl. No. 13/168,304.
USPTO Office Action dated Nov. 1, 2013 for copending U.S. Appl. No. 13/168,349.
USPTO Office Action dated Nov. 4, 2013 for copending U.S. Appl. No. 13/168,361.
USPTO Office Action dated Feb. 26, 2014 for copending U.S. Appl. No. 13/168,229.
USPTO Notice of Allowance dated Jun. 3, 2014 for co-pending U.S. Appl. No. 13/168,374.
USPTO Office Action dated Jun. 4, 2014 for co-pending U.S. Appl. No. 13/168,304.
USPTO Office Action dated Jun. 5, 2014 for co-pending U.S. Appl. No. 13/168,349.
USPTO Notice of Allowance dated Jun. 17, 2014 for co-pending U.S. Appl. No. 13/168,361.
Copending U.S. Appl. No. 14/337,544, filed Jul. 22, 2014; Daniel Latham Terrill et al.
USPTO Notice of Allowance dated Aug. 4, 2014 for co-pending U.S. Appl. No. 13/168,229.
Copending U.S. Appl. No. 14/459,875, filed Aug. 14, 2014; Damon Ray Billodeaux et al.
Copending U.S. Appl. No. 14/307,956, filed Jun. 18, 2014; Damon Ray Billodeaux et al.
USPTO Notice of Allowance dated Jul. 7, 2014 for co-pending U.S. Appl. No. 13/168,374.
USPTO Notice of Allowance dated Jul. 9, 2014 for co-pending U.S. Appl. No. 13/168,330.

\* cited by examiner

PRODUCTION OF HYDROXY ETHER HYDROCARBONS BY VAPOR PHASE HYDROGENOLYSIS OF CYCLIC ACETALS AND KETALS

1. FIELD OF THE INVENTION

The invention relates to the production of hydroxy ether hydrocarbons from the hydrogenolysis of cyclic acetals or cyclic ketals.

2. BACKGROUND OF THE INVENTION

Acetals and ketals are readily obtained by the reaction of aldehyde or ketone hydrocarbons and polyhydroxyl hydrocarbons by many methods well known in the art. There are many references to the efficient preparation of these materials. It is desirable to prepare 2-alkoxy-ethanol compounds, such as 2-n-butoxyethanol and 2-n-propoxyethanol without the requirement of using ethylene oxide as the reactant. It is also desirable to have a process which is robust enough to prepare other hydroxy ether compounds without the requirement of using other highly reactive epoxy compounds and similar materials such as propylene oxide, 1,2-epoxybutane, glycidol (2,3-epoxy-1-propanol) and trimethylene oxide. It is also desirable to prepare hydroxy ether compounds in high selectivity without requiring alkylating agents such as alkyl bromides, chlorides and sulfates in their reaction with polyhydroxyl compounds in a Williamson ether synthesis with the concurrent production of waste salts.

The classes of compounds known as hydroxy ether hydrocarbons have great value as solvents and dispersants for latex paints and other coatings. They also have value as components of industrial and consumer cleaning solutions and surfactants and raw materials for the preparation of polyurethane materials. The large bulk of this class of compounds that are commercially available are generally known as "E-series" and "P-series" solvents. The "E-series" solvents are prepared by the reaction of ethylene oxide (EO) with corresponding alcohols to form the "E-series" products. Conversely, the "P-series" of solvents are prepared by the reaction of propylene oxide (PO) with corresponding alcohols to form similar materials. This technology has a number of concerns and difficulties. First, ethylene oxide and propylene oxide are hazardous materials. Likewise, the nature of the reaction of an alcohol with highly reactive epoxides generates relatively low selectivity for desirable mono addition of EO or PO to the alcohol resulting in di-, tri and poly-EO or PO addition products in significant amounts. Third, the technology of mono ethylene glycol (MEG) production is moving away from the traditional isolation of ethylene oxide and subsequent reaction with water toward more efficient methods to prepare MEG in higher yield that use other technology, such as ethylene carbonate and direct water quenching of crude EO reactor product. These newer technologies remove a ready source of on-site EO for the production of E-series products. Fourthly, historically, a large capital intensive EO/MEG facility needs to be located in close proximity to the alcohol production facility to be efficient and avoid the risk of having to transport EO over long distances. In the case of "P-series" products, a propylene oxide unit also has to be conveniently located. The traditional preparation of PO involves the co-product formation of precursor materials leading to final products such as styrene and MTBE. Other methods to make PO have been developed, as for example, by the use of expensive hydrogen peroxide. The use of PO to make P-series materials thus has cost concerns and secondary co-product environmental concerns.

There is additionally a need to be able to make valuable hydroxy ether hydrocarbons from renewable resources without the need for EO or PO. Much recent work has been carried out to produce ethylene glycol and propylene glycol by the hydrogenolysis of sugars. A large scale process for making MEG and 1,2-propylene glycol (PG) from corn syrup has been commercialized in the People's Republic of China. Ethylene glycol is known to react readily with aldehyde compounds to form, for example, cyclic 2-alkyl-1,3-dioxolane compounds, a class of acetal compounds particularly suitable for the manufacture of hydroxy ether solvents. In a similar manner, 1,2-propylene glycol can form 4-methyl-1,3-dioxolane compounds and 1,3-propylene glycol can form 1,3-dioxane compounds.

Dioxolane compounds are characterized by having a five-membered ring with oxygen atoms in the 1 and 3 positions. Other materials based on renewable materials can also be used to prepare acetal compounds by known reactions with aldehydes, including glycerin, 1,3-propanediol and sugar-derived polyols such as mannitol, erythritol, 1,2- and 2,3-butanediol, and the like. In some of these other examples a class of acetal compound having a six-membered ring with oxygen atoms in the 1 and 3 positions known as 1,3-dioxanes can be prepared. Ketals, may also be prepared by the reaction of ketone hydrocarbons with the above poly hydroxyl hydrocarbons in a similar manner to that of the preparation of acetals.

Previous work has been disclosed in the literature that discusses the hydrogenolysis of acetals, both cyclic and open to produce ether type hydrocarbons. In the case of 1,3-dioxolane acetal compounds, work has been disclosed that describes the preparation of valuable 2-alkoxy ethanol compounds. This chemical transformation is carried out by the cleavage of the oxygen-carbon bond attached to the carbon in the 2-position of the ring with hydrogen using a noble metal catalyst. The focus of that work has been on the liquid-phase hydrogenolysis of acetals in a solvent that is typically the diol moiety used to prepare the cyclic acetal. The art teaches the importance of having a large excess of this diol solvent present during the hydrogenolysis reaction to prevent the formation of significant amounts of undesired co-product, namely a diether.

One example of this reaction is in the preparation of 2-n-butoxyethanol by the palladium catalyzed liquid-phase hydrogenolysis of 2-propyl-1,3-dioxolane in ethylene glycol solvent. A co-product diether compound, namely 1,2-dibutoxyethane, is formed in significant amounts if a large amount of excess ethylene glycol is not used. Diether co-product is particularly undesirable as the formation of one mole of diether consumes two moles of the acetal feed material and at the same time liberates a mole of ethylene glycol. The mole ratio of ethylene glycol to acetal compound has to be greater than 1/1 to produce the desired 2-n-butoxyethanol product in significant amounts. In most of the examples given, a mole ratio of 9/1 EG/acetal is used. This large excess of ethylene glycol solvent creates problems in a practical process by requiring its removal, such as by energy consuming distillation and large equipment required to handle the large volumes created by the use of large volumes of ethylene glycol solvent. Additionally, the use of phosphoric and other similar phosphorous-containing acid co-catalysts and hydroquinone type additives are disclosed as promoters in this process. The same strategy of using excess diol solvent is postulated in the liquid phase hydrogenolysis of acetals where other compounds, such as cyclic acetals prepared from 1,2 and 1,3-propanediol materials and solvents are used, if a favorable selectivity to the desired hydroxy ether product is to be attained. Examples are found in the literature where mixtures of aldehyde and polyhydroxyl hydrocarbons are used directly in a hydrogenolysis process to make the desired hydroxy ether products. In these latter examples, an even higher ratio of polyhydroxyl hydrocarbon/aldehyde is required to effect the desired reaction to prepare the desired hydroxy ether products efficiently. As can be seen from the available art, there is a definite need to be able to carry out the efficient catalytic hydrogenolysis of cyclic acetals to make desired hydroxy ether products, without the use of diol or polyhydroxyl hydrocarbon solvent.

3. SUMMARY OF THE INVENTION

We have surprisingly found that an efficient hydrogenolysis reaction can be carried out to transform cyclic compounds, including 1,3-dioxolane and 1,3-dioxane classes of compounds, with high selectivity to their 2-alkoxy-1-ethanol or 3-alkoxy-1-propanol type products, respectively, in a vapor phase reaction. The hydrogenolysis reaction of the invention is carried out in the vapor phase to produce the above classes of cyclic 1,3-dioxolane and 1,3-dioxane compounds using a supported noble metal catalyst. The selectivity to the 2-alkoxy-1-ethanol or 3-alkoxy-1-propanol type products is increased by elevating the temperature and controlling the pressure in the hydrogenolysis reaction sufficient to prevent the starting materials and/or the ether solvent products from dropping below their respective dew points.

There is now provided a process comprising contacting hydrogen with a cyclic compound composition comprising cyclic acetal compounds, cyclic ketal compounds, or a combination thereof in the vapor phase to produce a hydroxy ether hydrocarbon composition.

There is also provided a process of:
(a) feeding hydrogen and the cyclic compound composition to a reaction zone within a reaction vessel, and
(b) conducting a reaction in the reaction zone comprising contacting hydrogen with at least a portion of the cyclic compound composition in the reaction zone under reaction zone conditions above the dew point of the cyclic compound composition to produce hydroxy ether hydrocarbons, fed to the reaction zone, and
(c) withdrawing a product stream from the reaction zone comprising hydroxy ether hydrocarbons, hydrogen, and if present any unreacted cyclic compounds.

There is also provided a hydrogenolysis process comprising reacting cyclic compounds with hydrogen in a reaction zone over a noble metal catalyst in the absence of a liquid, such as a hydrocarbon co-solvent, in the reaction zone, wherein said cyclic compounds comprise cyclic acetals, cyclic ketals, or a combination thereof.

There is also now provided a process comprising contacting cyclic compounds in the vapor phase with hydrogen in a reaction zone to produce a vapor hydroxy ether hydrocarbon, wherein said cyclic compounds comprise cyclic acetals, cyclic ketals, or a combination thereof.

There is further provided a process comprising feeding hydrogen and cyclic compounds, comprising cyclic acetal compounds or cyclic ketal compounds, to a reaction zone and reacting hydrogen and the cyclic compounds in the presence of a noble metal catalyst and withdrawing from the reaction zone a product stream comprising hydroxy ether hydrocarbons, wherein said product stream withdrawn from the reaction zone contains less than 100 ppmw noble metal catalyst based on the weight of cyclic compounds fed to the reaction zone.

4. DETAILED DESCRIPTION OF THE INVENTION

As used herein, "cyclic compounds" includes cyclic acetal compounds, cyclic ketal compounds, and combinations thereof.

In the process of the invention, cyclic compounds in a cyclic compound composition are contacted with hydrogen in the vapor phase to produce hydroxy ether hydrocarbons. The cyclic compounds are in the vapor phase at least in the reaction zone and desirably also fed to the reaction zone in the vapor phase. For example, one may hydrogenate the cyclic compounds by:

(a) feeding hydrogen and a cyclic compound composition comprising cyclic compounds, and preferably a cyclic compound vapor composition, to a reaction zone within a reaction vessel, and (b) contacting at least a portion of the cyclic compound composition with hydrogen in the reaction zone under reaction zone conditions above the dew point of the cyclic compound composition fed to the reaction zone to produce hydroxy ether compounds in the reaction zone, and (c) withdrawing a product stream from the reaction zone comprising hydroxy ether hydrocarbons, hydrogen, and if present any unreacted cyclic compounds.

The cyclic compounds can be contacted with hydrogen in a reaction zone over a noble metal catalyst advantageously in the absence of a liquid, such as a solvent like ethylene glycol, in the reaction zone during the hydrogenolysis reaction. Also, advantageously, the noble metal catalyst does not need to be separated from the product stream effluent because the reaction proceeds in the vapor phase over a heterogeneous catalyst bed, preferably a fixed bed.

The cyclic compound composition of the invention contains cyclic compounds. The cyclic compounds that are contacted with hydrogen in the process of the invention are those having a cyclic acetal or ketal moiety. The cyclic acetal moiety produced in the process of the invention has two oxygen atoms single bonded to the same carbon atom in the ring structure. Examples include cyclic compounds having 1,3-dioxolane moieties and dioxane moieties (especially 1,3-dioxane moieties), as well as those having larger rings with oxygen atoms in the 1,3 position.

In one embodiment, the cyclic compound(s) may be represented by the general formula:

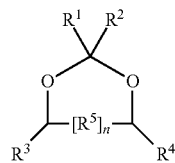

wherein $R^1$, $R^2$, $R^3$, and $R^4$ are independently H; an branched or un-branched $C_1$-$C_{50}$ alkyl, $C_2$-$C_{50}$ alkenyl, aryl-$C_1$-$C_{50}$ alkyl, aryl-$C_2$-$C_{50}$ alkenyl-, $C_3$-$C_{12}$ cylcoalkyl, or a $C_3$-$C_{50}$ carboxylate ester; and wherein the alkyl, alkenyl, aryl, and cycloalkyl groups of $R^1$, $R^2$, $R^3$, and $R^4$ are optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol;

and any one or both of $R^3$ and $R^4$ are optionally independently a hydroxyl, halogen, dialkylamino, amine, aldehyde, ketone, carboxylic acid, ester, ether, alkynyl, dialkylamide, anhydride, carbonate, epoxide, lactone, lactam, phosphine, silyl, thioether, thiol, or phenol;

and wherein $R^1$ and $R^2$ are not both H;

and $R^1$ and $R^2$ optionally together form a cycloalkyl having 3-12 carbon atoms;

and wherein $R^5$ is branched or unbranched, substituted or unsubstituted, divalent alkyl or divalent alkenyl group each having 1 to 8 carbon atoms and optionally containing 1, 2, or 3 oxygen atoms in the alkyl or alkenyl group;

and wherein n is an integer selected from 0 or 1.

$R^1$, $R^2$, $R^3$, and $R^4$ may independently be H, or a branched or un-branched $C_1$-$C_6$ alkyl group. Or, $R^1$, $R^2$, $R^3$, and $R^4$ may independently be H, or a branched or un-branched $C_1$-$C_4$ alkyl group. $R^1$ may be a branched or unbranched $C_1$-$C_6$ alkyl group while $R^2$ is a hydrogen atom.

$R^5$ may be a branched or unbranched divalent alkyl group having 1 to 6, or 1 to 4, or 1 to 3, or 1 to 2 carbon atoms.

Examples of cyclic acetals include 2-propyl-1,3-dioxolane, 2-propyl-1,3-dioxane, 2-ethyl-1,3-dioxolane, 2-ethyl-1,3-dioxane, 2-methyl-1,3-dioxolane, 2-methyl-1,3-dixoane, 2-propyl-4-methyl-1,3-dioxane, 5,5-dimethyl-2-propyl-1,3-dioxane, 5,5-dimethyl-2-ethyl-1,3-dioxane, 4-hydroxymethyl-2-propyl-1,3-dioxolane, 4-hydroxymethyl-2-propyl-1,3-dioxane, 2-ethyl-1,3-dioxepane, 2-ethyl-1,3,6-trioxocane.

As to substituents, in one embodiment, $R^3$ or $R^4$ is a hydroxyl group.

In the case one desires to use a cyclic acetal compound as a starting material, one of $R^1$ or $R^2$ is a hydrogen atom. $R^1$ and $R^2$ may independently be H, or a branched or un-branched $C_1$-$C_6$ alkyl group. Or, $R^1$ and $R^2$ may independently be H, or a branched or un-branched $C_1$-$C_4$ alkyl group. $R^1$ may be a branched or unbranched $C_1$-$C_6$ alkyl group while $R^2$ is a hydrogen atom. Particularly useful cyclic acetals for this invention leading to useful materials of commerce include 1,3-dioxolanes having $R^1$ being an alkyl group that can lead to "E-series" type solvents. Likewise, 1,3-dioxolanes having $R^1$ being an alkyl group and $R^3$ being a methyl group can lead to "P-series" type solvents.

In the case one desires to start with a cyclic ketal compound as the starting material, then neither $R^1$ nor $R^2$ are hydrogen atoms. $R^1$ and $R^2$ may independently be a branched or un-branched $C_1$-$C_6$ alkyl group. Or, $R^1$ and $R^2$ may independently be a branched or un-branched $C_1$-$C_4$ alkyl group. Other potentially useful acetals that make use of 1,3-propylene glycol and glycerin in their preparation would include 1,3-dioxane acetals having $R^1$ being an alkyl group and 1,3-dioxane acetals having $R^1$ being an alkyl group and $R^4$ being a hydroxyl group. A variation of the glycerin acetals that have potentially useful derivatives would be 1,3-dioxolane acetals having $R^1$ being an alkyl group and $R^3$ being a hydroxymethyl group.

Examples of cyclic acetals that have 1,3-dioxolane moieties include 2-propyl-1,3-dioxolane, 2-propyl-1,3-dioxolane, 2-ethyl-1,3-dioxolane, 2-methyl-1,3-dioxolane, 4-hydroxymethyl-2-propyl-1,3-dioxolane.

Examples of cyclic acetals that have 1,3-dioxane moieties include 2-propyl-1,3-dioxane, 2-ethyl-1,3-dioxane, 2-methyl-1,3-dixoane, 2-propyl-4-methyl-1,3-dioxane, 5,5-dimethyl-2-propyl-1,3-dioxane, 5,5-dimethyl-2-ethyl-1,3-dioxane, and 4-hydroxymethyl-2-propyl-1,3-dioxane.

Examples of cyclic ketals that can be utilized in the present invention include, but are not limited to, 2,2-dimethyl-1,3-dioxolane, 2,2-dimethyl-1,3-dioxane, 2,2,4-trimethyl-1,3-dioxolane, 2,2-dimethyl-1,3-dioxepane, 2,2-dimethyl-1,3,6-trioxocane, 4-methanol-2,2-dimethyl-1,3-dioxolane, 2,2-dimethyl-1,3-dioxan-5-ol, 2,2,5,5-tetramethyl-1,3-dioxane, 2-ethyl-2-methyl-1,3-dioxolane, 2-ethyl-2-methyl-1,3-dioxane, 2-ethyl-2,4-dimethyl-1,3-dioxane, 2-ethyl-2-methyl-1,3-dioxepane, 2-ethyl-2-methyl-1,3,6-trioxocane, 2-ethyl-2,5,5-trimethyl-1,3-dioxane, 4-methanol-2-ethyl-2-methyl-1,3-dioxolane, 2-ethyl-2-methyl-1,3-dioxan-5-ol, 2-methyl-2-propyl-1,3-dioxolane, 2-methyl-2-propyl-1,3-dioxane, 2,4-dimethyl-2-propyl-1,3-dioxane, 2-methyl-2-propyl-1,3-dioxepane, 2-methyl-2-propyl-1,3,6-trioxocane, 2,5,5-trimethyl-2-propyl-1,3-dioxane, 4-methanol-2-methyl-2-propyl-1,3-dioxolane, 2-methyl-2-propyl-1,3-dioxan-5-ol, propyl-1,3-dioxolane, 2-methyl-2-pentyl-1,3-dioxolane, 2-methyl-2-pentyl-1,3-dioxane, 2,4-dimethyl-2-pentyl-1,3-dioxane, 2-methyl-2-pentyl-1,3-dioxepane, 2-methyl-2-pentyl-1,3,6-trioxocane, 2,5,5-trimethyl-2-pentyl-1,3-dioxane, 4-methanol-2-methyl-2-pentyl-1,3-dioxolane, and 2-methyl-2-pentyl-1,3-dioxan-5-ol.

The cyclic acetals and ketals are prepared by reacting a polyhydroxyl compound with a carbonyl functional compound that is either an aldehyde or a ketone, in the present of an acid catalyst.

The cyclic acetals and ketals are prepared by reacting a polyhydroxyl compound with a carbonyl functional compound that is either an aldehyde or a ketone, in the present of an acid catalyst.

The polyhydroxyl compounds have at least two hydroxyl (—OH) functionalities. The polyhydroxyl compounds may contain ether or ester linkages in the longest carbon chain.

Suitable polyhydroxyl compounds for the present invention include, but are not limited to ethylene glycol, 1,2-propanediol, 1,3-propanediol, 1,4-butanediol, 1,3-butanediol, 1,2-butanediol, 1,2-pentanediol, 2,4-pentanediol, 2,2-dimethyl-1,3-propanediol, diethyleneglycol, and triethyleneglycol, glycerin, trimethylolpropane, xylitol, arabitol, 1,2- or 1,3cyclopentanediol, 1,2- or 1,3-cyclohexanediol, and 2,3-norbornanediol.

The carbonyl compounds contain at least one carbonyl functionality. In the present invention, any carbonyl compound may be used.

For example, the carbonyl compound is represented by the formula:

$R^1R^2C{=}O$ in which $R^1$ and $R^2$ are independently H, $C_1$-$C_{50}$ alkyl, $C_2$-$C_{50}$ alkenyl, aryl-$C_1$-$C_{50}$ alkyl, aryl-$C_2$-$C_{50}$ alkenyl-, or $C_3$-$C_{12}$ cylcoalkyl, and wherein the alkyl, alkenyl, aryl, and cycloalkyl groups of $R^1$ are optionally saturated or unsaturated, and branched or unbranched or substituted or unsubstituted with 1, 2, or 3 groups comprising —OH, halogen, dialkylamino, $C_1$-$C_6$ alkyl, aldehyde, ketone, carboxylic acid, ester, ether, alkynyl, dialkylamide, anhydride, carbonate, epoxide, lactone, lactam, phosphine, silyl, thioether, thiol, aryl, phenol, or combinations thereof. $R^1$ and $R^2$ optionally together form a cycloalkyl having 3-12 carbon atoms;

When one of $R^1$ and $R^2$ is hydrogen, the carbonyl compound is an aldehyde compound. The aldehyde compound may have, if desired, at least one aldehyde functional group wherein the aldehyde carbon atom is bonded to a (i) branched or unbranched $C_1$-$C_9$ alkyl group or (ii) an aryl or alicyclic group which is optionally substituted with a branched or unbranched $C_1$-$C_9$ alkyl group.

Examples of an aldehyde compounds include, but are not limited to, benzaldehyde, formaldehyde, acetaldehyde, propionaldehyde, butyraldehyde, isobutyraldehyde, pentaldehyde, 2-methylbutyraldehyde, 3-methylbutyraldehyde, n-pentanal, isopentanal, hexyldehyde, heptaldehyde, 2-ethylhexyldehyde, octanal, nonanal, n-decanal, 2-methylundecanal, lauryl aldehyde, myristyl aldehyde, cetyl aldehyde, stearyl aldehyde, behenyl aldehyde, glutaraldehyde, acrolein, crotonaldehyde, oleyl aldehyde, linoleyl aldehyde, linolenyl aldehyde, erucyl aldehyde, cinnamaldehyde, 1,3-cyclohexanedicarboxaldehyde, 1,4-cyclohexanedicarboxaldehyde, and combinations thereof.

When neither $R^1$ nor $R^2$ is hydrogen, the carbonyl compound is a ketone. Examples of suitable ketone compounds include, but are not limited to, acetone, methyl isobutyl ketone (2-butanone), methyl ethyl ketone, methyl propyl ketone (2-pentanone), methyl isopropyl ketone (3-methyl-2-butanone), methyl isobutyl ketone (4-methyl-2-pentanone), 2-hexanone, cyclohexanone, 2-heptanone (methyl amyl ketone), 4-heptanone, and 2-octanone.

The starting feed materials used in the process of the invention comprise cyclic acetal compounds or cyclic ketal compound or combinations thereof. The process of the invention is a vapor phase reaction conducted at an elevated pressure. Therefore, the feed materials selected should be sufficiently volatile to enter the reaction vessel in a gaseous state as a gaseous feed stream. Accordingly, the feed materials must have a pure liquid vapor pressure of at least 1 mm Hg (0.133 kPa) (at the reaction temperature). To obtain better reaction rates, it is desired to select a feed material that has a vapor pressure in excess of 10 mm Hg (1.33 kPa).

For example, feed material compounds with relatively high boiling points like a cyclic acetal or ketal compound can be selected with high boiling points (at 1 atm) in excess of 200° C. or even at least 250° C. (523 degrees K.) because those same compounds may have practical vapor pressures of in excess of 50 mm Hg or at least 70 mm Hg (9.33 kPa) at typical hydrogenolysis reaction temperatures (at least 150° C., or at least 180° C. or at least 190° C. or at least 200° C.) in the reaction vessel.

The process has the ability to be operated at a wide range of reaction temperature conditions. Suitable reaction temperatures (reactor set points) range from at least 100° C., or at least 130° C., or at least 150° C., or at least 170° C., or at least 180° C., or at least 190° C., or at least 200° C., or at least 210° C., or at least 220° C., and up to 300° C., or up to 275° C., or up to 250° C., or up to 240° C., or up to 230° C., or up to 220° C., or up to 210° C., or up to 200° C.

The favored temperature range for the practice of the invention is at least 150° C. because reaction rates increase at higher temperatures and up to about 250° C. Temperatures in excess of 250° C. start to suffer from excessive side product reactions. Suitable ranges include 190° to 250° C., or 200° to 230° C.

We have found that the efficiency of the process is increased if the operating reaction conditions are at temperatures above the dew point of the cyclic compound composition in the gaseous feed stream at reaction pressure. In another embodiment, the operating reaction conditions are at a temperature above the dew point of both the cyclic compound composition and the reaction products of the cyclic acetals in the gaseous product stream.

Dew point is defined as the temperature and pressure at which liquid condensation begins to take place for a gaseous mixture having a condensable material. See Dictionary of Scientific and Technical Terms published by McGraw-Hill, Fifth Edition, 1994. In practice, dew point is controlled by a combination of factors. The first factor is the actual vapor pressure of a pure liquid as a function of temperature. Increasing temperature increases the vapor pressure of a pure liquid thereby making it less likely to condense at higher temperature. Cyclic acetals and ketals behave in this manner. Lowering the temperature also lowers the vapor pressure of the liquid. Thus, operating the reaction at lower temperatures will require lowering the pressure in the reaction vessel to prevent the cyclic acetals from dropping below their dew point. It is desirable to conduct the hydrogenolysis at elevated temperatures in order to keep materials from condensing into a liquid phase at reaction conditions.

The second factor that keeps the cyclic compounds in the gaseous state and prevents them from dropping below their dew points is to keep the reactor absolute pressure low enough to keep the actual partial pressure of the component cyclic acetals above the dew point in the gaseous feed. The partial pressure of the cyclic acetals is related to the vapor pressure of the pure compounds at reaction temperature. Partial pressure (PP) of a given component "b" is defined: P(absolute)×(mole fraction of b in the mixture). Mole fraction is the portion of moles of the component in the total moles of a mixture. The partial vapor pressures of organic materials in this invention at reaction pressure and temperature must remain below the vapor pressure of the pure materials at that reaction temperature to avoid condensation. In essence, lowering reactor absolute pressure of a given mole fraction of reactant cyclic acetal in the feed will thereby lower the partial pressure of the reactant cyclic acetal. The vapor pressures of pure materials may be obtained by normal calculations with established physical constants or obtained from vapor pressure tables. For example one such method of vapor pressure calculation for the pure compound 2-n-propyl-1,3-dioxolane (PDX) would be: vapor pressure of PDX in mm Hg=10**((−0.2185×(A/K)+B) where A=10183.9; K=Temperature of the PDX in degrees Kelvin; and B=+8.363358. Thus the vapor pressure of pure PDX would be about 4560 mm Hg (607.95 kPa) at 200 degrees Celsius (473 degrees K.).

Without being bound to a theory, not having liquid condensation on the surface of the supported noble metal catalyst facilitates the transfer of gaseous hydrogen into the catalytic cycle. Indeed, we have found improvement in catalyst performance when progressively lower partial pressures of organic reactants are used at a given reactor temperature and pressure.

The hydrogenolysis reaction uses hydrogen as both a gaseous feed medium and reactant in this invention. A hydrogenolysis reaction uses hydrogen to cleave the carbon-oxygen bond of either the 1,2 carbon-oxygen bond or the 2,3-carbon-oxygen bond by means of the supported noble metal catalyst. The purity of the hydrogen being fed to the reactor is high enough to effect the desired reaction and not contain significant amounts of impurities that could act as poisons or inhibitors. Inert hydrocarbons such as methane, ethane, propane and butane are managed by normal gas purging methods to keep the desired partial pressure of reactant hydrogen present in the reactor. For certain impurities such as carbon monoxide, methods such as nickel methanation catalyst beds and the like can be used to convert this poison into an inert methane impurity and thereby control the concentration of CO in the reactor feed stream.

The amount of hydrogen fed in the continuous process can be that amount sufficient to enhance conversion of the cyclic compound, and is desirably set to an amount which is also conducive to maintain or increase selectivity toward the desired hydroxy ether hydrocarbon. The amount of hydrogen used will vary depending on the reaction conditions and type of cyclic compound used as the substrate, but generally, a molar ratio of hydrogen to cyclic compound of at least 5:1 is suitable. Other examples of molar ratios of hydrogen to cyclic compounds include at least 10:1, or at least 50:1, or at least 100:1, or at least 150:1, or at least 170:1, or at least 190:1, or at least 200:1, or at least 250:1, and can be as high as desired.

The reactor pressures used may be from one atmosphere absolute (or 0 psig or 0 kPa gauge), or from at least 5 atm, or from at least 8 atm, or from at least 10 atm, or from at least 12 atm, or from at least 13 atm, or from at least 15 atm, or from at least 20 atm (about 300 psig), or at least 28 atm (400 psig) and up to 141 atmospheres (2000 psig), or up to 105 atmospheres (1500 psig), or up to 88 atmospheres (1250 psig), or up to 69 atmospheres (or 1000 psig, or 6895 kPa) or up to 51 atmospheres (or 750 psig, or 5171 kPa gauge), or), or up to 45 atm, or up to 40 atm, or up to 35 atm, or up to 30 atm, or up to 27 atm, or up to 25 atm, or up to 10 atm. Suitable reactor pressures can range from at least 10 atm, or at least 13 atm, and up to 141 atm, or up to 105 atm, or up to 88 atm. One example of a suitable range is from 13 atm to 141 atm (200 to 2000 psig), or 20 atm (300 psig to 88 atm (1250 psig), for many practical operations.

The reactor design is not crucial for the operation of this invention. The reactor should be designed to permit a gaseous mixture of hydrogen and the cyclic compounds to pass over the supported noble metal catalyst and exit the reactor zone with the desired hydroxy ether hydrocarbon as a gaseous product mixture. Convenient designs include plug flow reactors such as long tubular designs and multi-tube short path designs. Other reactors known as "pancake" reactors have a wide continuous catalyst bed that is of a relatively short path. The process can also be conducted in exotic designs such as spinning basket or Berty type reactors can be used. In all reactor designs, however, the catalyst bed should remain at a temperature above the dew point of the reactants and products at the reactor conditions used. Additionally, the design of the reactor feed system should be designed to keep the feed composition compositionally balanced to that the partial pressures of the cyclic compounds fed to the reactor remain above the dew points of the cyclic compounds under the operating reactor conditions. This may be easily achieved by use of vapor liquid equilibrium feed chambers or by controlling the rates of liquid and hydrogen feed rate to the reactor via a mixing chamber to assure complete vaporization of the cyclic compounds at the reactor conditions prior to contact with the hydrogenolysis catalyst bed and to maintain the cyclic compounds at the proper feed partial pressure.

To our surprise we have found, unlike the examples given in the liquid phase hydrogenolysis of acetals, no polyhydroxyl hydrocarbon co-solvent feed, such as ethylene glycol, is required in a vapor phase hydrogenolysis conversion process. Thus, an advantage of the current process is conducting a conversion of cyclic compounds to their corresponding hydroxy ether hydrocarbon reaction products in the absence of a liquid solvent feed, such as ethylene glycol, at high selectivities.

For example, the selectivity of the converted compounds to any single type of hydroxy ether hydrocarbons (and not the by-product) using the vapor phase hydrogenolysis process on a molar basis can be at least 85%, or at least 90%, or at least 93%, or at least 95%, or at least 96%, or at least 97%, or at least 98%, and up to less than 100%, or up to less than 99%.

The conversion rates from the cyclic compounds to any and all converted reaction products can be at least 35%, or at least 75%, or at least 90%, or at least 92%, or at least 94%, or at least 95%.

A large number of supported noble metal catalysts can be employed in this invention and are preferred over base metal catalysts such as reduced nickel, copper or cobalt. We have also found that of the noble metals, palladium is most desirable for use in this invention although other noble metals like Ru, Rh, Pt, Ir, and Os may be used in varying degrees of effectiveness. The nature of the support and the degree of metal dispersion, as relating to metal particle size, and as controlled by the combination of weight percent metal loading in concert with catalyst support surface area, affects the catalytic activity and percent selectivity of the converted acetal or ketal into the desired hydroxy ether hydrocarbon product. Of the noble metals, palladium is most preferred Suitable metal catalyst loading may range from 0.1% by weight up to 5% by weight with a range of 0.25% by weight up to 1% by weight also being a useful range.

The support for the metal catalyst is not particularly limited and any known support can be used. Examples of suitable supports include alumina, silica, aluminum oxide, activated carbon, zirconia, titania, spinel, classes of oxides, and magnesium oxide.

The surface area of the support is not limited. Those having low surface area are effective to increase the selectivity to obtain the desired hydroxy ether hydrocarbon. Suitable surface areas for the support are within a range of 5-300 m$^2$/g. Surprisingly, noble metal catalysts, such as palladium, dispersed on aluminum oxide (e.g. α-aluminum oxide support) and zirconium oxide supports with low surface area are very selective for obtaining a hydroxy ether hydrocarbon product, often in greater than 95% molar selectivity from the converted cyclic compound feed material. The surface area of the aluminum oxide or zirconium oxide support is less than 300 m2/g, or up to 200 m2/g, or up to 150 m2/g, or up to 100 m2/g, or up to 75 m2/g, and at least 1 m2/g, or at least 5 m2/g, or at least 50 m2/g, or at least 75 m2/g, or at least 100 m2/g. Those with a surface area within a range of 5 m2/g to 150 m2/g, or 5 m2/g to 100 m2/g are also suitable and provide good selectivity.

Noble metals such as palladium dispersed on alumina, silica, activated carbon and other supports are suitable. We have found alumina and zirconium oxide supports with a palladium loading in the 0.20 to 0.6 weight % range generally yield catalysts that reduce the formation of co-products such as diether compounds, ester compounds and other by-products that result from unselective reactions upon the cyclic compound feed and by secondary decomposition of liberated ethylene glycol, a co-product of diether formation.

A support which can increase selectivity is an aluminum oxide (e.g. α-aluminum oxide support) or a zirconium oxide support. High purity aluminum oxide supports having low content of SiO$_2$ are preferred. Aluminum oxide supports having an alpha aluminum content of at least 98 wt % or at least 99 wt % are desirable. Also those having a SiO$_2$ content of up to 0.5 wt %, or up to 0.3 wt %, or up to 0.2 wt %, or up to 0.1 wt % are effective at increasing selectivity.

The process of the invention can also take place in the presence of a catalyst with low loading and with a support having low surface area. Thus, the process of the invention can also employ a catalyst that is a noble metal catalyst, such as a palladium metal, supported on aluminum oxide or zirconium oxide, wherein the degree of noble metal loading is lower than 5 wt. %, or up to 1 wt. %, or up to 0.6 wt. % and greater than 0.1 wt. %, or at least 0.2 wt %, and the surface area of the aluminum oxide or zirconium oxide support is less than 300 m2/g, or up to 200 m2/g, or up to 100 m2/g, or up to 20 m2/g, or up to 15 m2/g, or up to 10 m2/g, or up to 8 m2/g, or up to 6 m2/g, and at least 1 m2/g, or at least 2 m2/g, or at least 3 m2/g. Those with a surface area within a range of 1-20 m2/g, or 2-10 m2/g, or 3-7 m2/g are also suitable and provide good selectivity.

Desirable are catalysts having a combination of features that are selective for obtaining the desired hydroxyl ether hydrocarbon product, often in greater than 90% molar selectivity from the converted acetal feed material. Such catalyst compositions include:

A. catalyst compositions comprising palladium metal supported on aluminum oxide or zirconium oxide having relatively low surface area, a low weight percentage loading of palladium, and a low silica content and B. catalyst compositions comprising palladium metal supported on aluminum oxide or zirconium oxide doped with an alkali metal comprising K, Na, Rb, of Cs; an alkaline earth metal, or a triphosphine oxide compound.

Category A

In this category, the surface area of the supports in the catalyst composition is relatively low. The low surface area of the support is effective to increase the selectivity to obtain the desired hydroxy ether hydrocarbon. The specific surface area most effective will depend on the type of support employed as well as the phase content of the support.

Aluminum oxide has many phases. Suitable phases include alpha, gamma, theta, and delta. For some catalyst compositions of the invention, the phases include the alpha and gamma phases. Each of these phases and their characterization are well known. For example, the α-alumina (alpha) phase has a hexagonal crystal structure which is the most thermodynamically stable form. γ-alumina (gamma) typically has a cubic crystal structure which is also stable at the operating temperatures of the invention. θ-alumina (theta) crystal structure can be characterized as typically having a monoclinic crystal structure, although the crystal structure can vary depending on the calcining temperature. The crystal structure of these forms are known and described in, for example, Kirk Othmer Encyclopedia of Chemical Technology, Volume 2, pages 302-317 (1992).

An α-aluminum oxide support desirably contains more than 95% of its crystal phases in the alpha phase. These ultrapure alpha phase aluminum oxide supports are desirable. Such high purity supports contain at least 97%, or at least 98%, or at least 99% of their phases in the alpha phase. α-aluminum oxide supports that have less than 90% alpha phase content often also contain high amounts of silicon oxide. Alumina supports with high contents of silicon oxide impact the selectivity of the catalyst toward the production of the desired hydroxy ether mono-hydrocarbon. γ-alumina supports have a gamma phase content of at least 95%, or at least 96%, or at least 97%, or at least 98%, or at least 99%. θ-alumina supports have a theta phase content of at least 95%, or at least 96%, or at least 97%, or at least 98%, or at least 99%. Like the alpha phase aluminum oxide supports, silicon oxides such as silicon dioxide poison the selectivity of the catalyst toward the production of hydroxy ether mono-hydrocarbon compounds.

The BET surface area (determined by the BET method by nitrogen adsorption to DIN 9277) of the aluminum oxide or zirconium oxide support are as follows:

(i) for α-aluminum oxide supports, less than 30 m2/g, or less than 25 m2/g, or up to 20 m2/g, or up to 15 m2/g, or up to 10 m2/g, or up to 8 m2/g, or up to 6 m2/g, and at least 0.1 m2/g, or at least 0.2 m2/g, or at least 0.5 m2/g. or at least 1 m2/g, or at least 2 m2/g. or at least 3 m2/g. Those with a surface area within a range of 0.1-30 m2/g, or 0.2-30 m2/g, or 0.2-15 m2/g are also suitable and provide good selectivity; and (ii) for γ-aluminum oxide, less than 350 m2/g, or less than 300 m2/g, and at least 100 m2/g, or at least 150 m2/g, or at least 200 m2/g. Those with a surface area within a range of 100-350 m2/g, or 150-300 m2/g, or 200-300 m2/g are also suitable and provide good selectivity; and (iii) for zirconium oxide supports, up to 100 m2/g, or up to 85 m2/g, or up to 80 m2/g, or up to 75 m2/g, or up to 70 m2/g, or at least 0.2 m2/g, or at least 0.5 m2/g, or at least 1 m2/g, or at least 5 m2/g, or at least 10 m2/g, or at least 15 m2/g, or at least 20 m2/g, or at least 25 m2/g, or at least 30 m2/g, or at least 35 m2/g. Those with a surface area within a range of 1-100 m2/g, or 10-90 m2/g, or 25-70 m2/g are also suitable and provide good selectivity.

Aluminum oxide and zirconium oxide supports with a low weight percentage of palladium loading generally yield catalysts that reduce the formation of byproducts such as diether compounds, ester compounds and other by-products that result from unselective reactions upon the cyclic compound feed and by secondary decomposition of liberated ethylene glycol, a co-product of diether formation. Suitable palladium metal catalyst loadings for these catalysts are at least 0.1 wt %, or at least 0.15 wt %, or at least 0.2 wt %, or at least 0.3 wt %, or at least 0.35 wt %, or at least 0.4 wt %, and up to or less than 2.0 wt %, or up to 1.5 wt %, or up to 1.0 wt %, or up to 0.8 wt %, or up to 0.7 wt %, or up to 0.6 wt %, or up to 0.5 wt %. Examples of suitable ranges include 0.1 wt % to 1.0 wt %, or 0.2 wt % to 0.7 wt %, or 0.2 wt % to 0.6 wt %.

Palladium can be loaded onto the supports by any conventional means. Palladium can be added as a metal or as a compound, such as palladium chloride, palladium chloride dihydrate, palladium bromide, palladium iodide, palladium oxide, or an organic palladium salt or complex such as palladium formate, palladium acetate, palladium butyrate and palladium acetylacetonate.

The catalyst compositions of the invention also have a low silicon dioxide content. Supports having a high silicon dioxide content have been found to reduce the selectivity and yield to the product of hydroxy ether mono-hydrocarbon compounds. The supports for the catalysts should have a SiO2 content of no more than 1.0 wt %, or less than 0.5 wt %, or less than 0.3 wt %, or no more than 0.2 wt %, or no more than 0.1 wt %. Those with low contents of silicon dioxide are effective at increasing selectivity.

The catalyst compositions in this Category A are those that have a moderate level of activity, that is, those which do not cause extremely high conversions of the cyclic compound feed across the catalyst. Moderate activity catalysts, that is, those that yield a conversion of the cyclic compound of at least 15%, or at least 20%, and up to 90%, or up to 85% (e.g. 15-90%, or 15-85%, or 20-90%, or 20-85%) generally yield the best selectivity to the desired hydroxy ether hydrocarbon. Low activity catalysts, yielding conversions of the cyclic compound below 20%, are not as desirable due to the inherent inefficiency of requiring a large amount of acetal recovery for recycle and in most cases also having a poor selectivity to the desired hydroxy ether hydrocarbon product based on converted cyclic acetal. The selectivity to the desired hydroxy ether mono-hydrocarbon suffers when the conversion activity of the catalyst is greater than 85%. While catalysts can be used outside these ranges and are within the scope of this invention, those having a activity of conversion of cyclic compounds from 20% to 85% are preferred.

Category B

We have also found that the aluminum oxide (in any phase, including but not limited to α, δ, γ phases) and zirconium oxide supports loaded with palladium and doped with alkali metals (Li, Na, K, Rb, Cs), other than lithium acetate, and alkaline earth metals (Mg, Ca, Sr, Ba) will increase the selectivity of converted acetal into desired products, or at least with a reduction in byproducts that have no utility, with some of the very active but relatively unselective catalyst systems. In these cases, the surface area of the catalyst supports are not particularly limited and the catalyst loading is also not particularly limited. While these dopants can be used on any of the catalyst compositions in Category A, the effects of these particular dopants are quite marked with the use of highly active catalysts that require improvement in selectivity. Although some of the dopants may actually decrease the activity of the catalyst, this is quite acceptable in the process of the invention because unconverted cyclic compounds can be recycled and subjected to further hydrogenolysis reactions.

Efforts at improving the selectivity of the highly active catalysts were not promising when candidates such as phosphoric acid and lithium acetate were investigated. We have found, however, that the specific dopants mentioned above were effective at improving selectivity of these active catalysts.

The alkali or alkaline earth metal or metals deposited onto the catalyst supports may have an oxidation state of other than zero. The supports may also be doped with alkali metal salts, other than lithium acetate, or alkaline earth metal salts. Suitable salts of alkali metals and alkaline earth metals include organic anions, such as C1-C8 carboxylates and halides such as acetate, chloride and fluoride salts, to increase the selectivity of converted acetal into desired products with some of the very active but relatively unselective catalyst systems. In addition to the alkali metals and alkaline earth metals, compounds containing organophosphine oxide moieties will also modify the selectivity of very active catalyst systems to suppress certain undesired diether co-product formation.

Specific examples of such modifiers used to dope the supports include potassium acetate, sodium acetate, barium acetate, calcium acetate, lithium fluoride, sodium fluoride, sodium chloride, potassium fluoride, potassium chloride, calcium fluoride, calcium chloride, magnesium acetate, magnesium fluoride, magnesium chloride, with potassium acetate, barium acetate, potassium fluoride, and sodium fluoride being preferred.

The dopants can be added to the catalyst supports by any conventional technique. One common technique for the impregnation of catalysts with dopants is the incipient wetness method.

The dopant is dissolved in a suitable solvent, in many cases being deionized water. The catalyst is added to the solution and the amount of solution is sufficient to wet the entire surface of the catalyst without any liquid remaining so as to disperse all the salts onto the support. The solvent is then evaporated leaving the salt dispersed onto the support and in the pores of the support. Vacuum can be applied and the supports agitated to assist migration of the salts into the pores of the support.

The triorganophosphine oxide compound can be monotriorganophosphine oxides or bis-triorganophosphine dioxide compounds. They can be represented by the general formula:

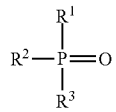

wherein R1, R2, and R3 are independently a branched or unbranched, substituted or unsubstituted alkyl group, aryl group, alicyclic group, or alkylaryl group each having from 1 to 20 carbon atoms, or any one of the R groups may be a bridging group having the following general formula:

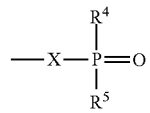

wherein X is a bridging group to form a bis-triorganophosphine dioxide and can be a branched or unbranched, substituted or unsubstituted alkyl group, aryl group, alicyclic group, or alkaryl group each having from 1 to 20 carbon atoms, and R4 and R5 can be selected from any of the groups of R1, R2, or R3 mentioned above.

Examples of phosphine oxides include without limitation butyldiethylphosphine oxide, butyldimethylphosphine oxide, butyldiphenylphosphine oxide, butyldipropylphosphine oxide, decyldiethylphosphine oxide, decyldimethylphosphine oxide, decyldiphenylphosphine oxide, dibutyl (2-methylphenyl)-phosphine oxide, diethyl(3-methylphenyl)-phosphine oxide, ethyldioctylphosphine oxide, ethyldibutylphosphine oxide, ethyldimethylphosphine oxide, ethyldiphenylphosphine oxide, ethyldipropylphosphine oxide, heptyldibutylphosphine oxide, heptyldiethylphosphine oxide, heptyldimethyl phosphine oxide, heptyldipentylphosphine oxide, heptyldiphenylphosphine oxide, hexyldibutylphosphine oxide, hexyldiethylphosphine oxide, hexyldimethyl phosphine oxide, hexyldipentylphosphine oxide, hexyldiphenylphosphine oxide, methylbis(4-methylphenyl)-phosphine oxide, methyldibutylphosphine oxide, methyldidecylphosphine oxide, methyldiethylphosphine oxide, methyldiphenylphosphine oxide, methyldipropylphosphine oxide, octyldimethylphosphine oxide, octyldiphenylphosphine oxide, pentyldibutylphosphine oxide, pentyldiethylphosphine oxide, pentyldimethylphosphine oxide, pentyldiphenylphosphine oxide, phenyldibutylphosphine oxide, phenyldiethylphosphine oxide, phenyldimethylphosphine oxide, phenyldipropylphosphine oxide, propyldibutylphosphine oxide, propyldimethylphosphine oxide, propyldiphenylphosphine oxide, tris(2,6-dimethylphenyl)-phosphine oxide, tris(2-methylphenyl)-phosphine oxide, tris (4-methylphenyl)-phosphine oxide, tris[4-(1,1-dimethylethyl) phenyl]-phosphine oxide, (1-methylethyl)diphenylphosphine oxide, 4-(diphenylmethyl)phenyl]diphenylphosphine oxide, bis(2-methylphenyl)(2-methylpropyl)-phosphine oxide, tributylphosphine oxide, tripropylphosphine oxide, triisopropylphosphine oxide, triethylphosphine oxide, triheptylphosphine oxide, trimethylphosphine oxide, trioctylphosphine oxide, tripentylphosphine oxide, tripropylphosphine oxide, triphenylphosphine oxide, tri-(o-tolyl)phosphine oxide, tri-(p-tolyl)phosphine oxide, tri-(m-tolyl)phosphine oxide, tri-(o-chlorophenylphosphine oxide, tri-(p-chlorophenyl)phosphine oxide, tri-(m-chlorophenyl)phosphine oxide, tricyclohexyl phosphine oxide, tribenzylphosphine oxide, dimethyl phosphine oxide, tri-2-methyl propyl phosphine oxide, dimethyldodecylphosphine oxide, 10 dimethyltetradecylphosphine oxide, methylethyltetradecylphosphine oxide, dimethylhexadecylphosphine oxide, dimethyloctadecylphosphine oxide, ethylpropylhexadecylphosphine oxide, diethyldodecylphosphine oxide, diethyltetradecylphosphine oxide, dipropyldodecylphosphine oxide, bis(2-hydroxyethyl)dodecylphosphine oxide, bis-(3-hydroxypropyl)-dodecylphosphine oxide, 20 methyl-2-hydroxypropyltetradecylphosphine oxide, dimethyloleylphosphine oxide, dimethyl-2-hydroxydodecylphosphine oxide, bis(hydroxymethyl)-dodecylphosphine oxide, diethyl-l-hydroxydodecylphosphine oxide, tetraphenyl dimethylene diphosphine dioxide(diphosdioxide), tetraphenyl trimethylene diphosphine dioxide, bis(diphenylphosphino)methane dioxide, 1,2bis(diphenylphosphino)ethane dioxide, 1,3bis(diphenylphosphino)propane dioxide, 1,4bis(diphenylphosphino)butane dioxide; 1,1'bis(diphenylphosphino)ferrocene dioxide, 1,2-bis(di(pentafluorophenyl)phosphino)ethane dioxide, bis(diphenylphosphinoefhyl)phenyl phosphine dioxides, or combinations thereof.

One example of a catalyst composition is a catalyst comprising an aluminum oxide support on which is deposited:
(i) palladium in an amount of up to 1 wt %, and
(ii) a modifier, other than lithium acetate, comprising an alkali metal, alkaline earth metal, or a organophosphine oxide compound.

Another example of such a new catalyst composition is a catalyst comprising a zirconium oxide support containing or on which is deposited.
(i) palladium in an amount of up to 1 wt %, and
(ii) a modifier, other than lithium acetate, comprising an alkali metal, alkaline earth metal, or an organophosphine oxide compound.

In each of these examples, the type of support and BET surface area of the support may be as described in each of the examples given in Category A. but are not limited to those surface areas. However, the dopants are effective also at improving the selectivity of the catalyst compositions beyond the surface areas described in Category A. The dopants are effective modifiers for highly active catalysts, and those would include compositions having high surface area and high loadings of palladium. Thus, the surface area and palladium loading are not particularly limited in this embodiment. Suitable surface areas of the doped supports are not limited, and can include those having a BET surface area ranging from 1 to 350 m2/g. Suitable loading of palladium ranges from 0.1 wt % up to 5 wt %, or up to 4 wt %, or up to 3 wt %, or up to 2 wt %.

In each of these examples in Category B, the support may contain or have deposited onto the support an alkali metal salt, other than a lithium salt, or an alkaline earth metal salt of C1-C8 carboxylates, chlorides, or fluorides. In each of these examples, the support may contain or have deposited onto the support potassium acetate, sodium acetate, barium acetate, calcium acetate, lithium fluoride, sodium fluoride, sodium chloride, potassium fluoride, potassium chloride, calcium fluoride, calcium chloride, barium chloride, magnesium acetate, magnesium fluoride, magnesium chloride, with potassium acetate, barium acetate, and sodium fluoride being preferred.

The catalysts may be additionally doped with other modifiers, including those that do not increase selectivity. It is desirable, however, to avoid the presence of additional dopants which decrease selectivity, retard the activity of the catalyst, do not appreciably increase yield, or are difficult to remove and process. Modifier additives such as dimethyl disulfide added to the catalyst and similar diorganic disulfides, hydrogen sulfide, carbonyl sulfide, triorganophosphines such as triphenylphosphine, lead salts, silver salts, tin salts, and controlled concentrations of carbon monoxide in the gaseous feed are examples of known methods to modify the activity of very active catalysts to be more selective.

Specific examples of useful alumina catalysts include Evonik Degussa 0.5% Pd/$\frac{1}{16}$" alumina spheres, Calsicat (Mallinckrodt Specialty Chemical Co.) 0.5% Pd/$\frac{1}{16}$"alumina spheres, Engelhard (BASF) 0.3% Pd/$\frac{1}{8}$" alumina spheres, Engelhard 2% Pd/$\frac{1}{8}$"silica "star" extrudates with MgO binder, Engelhard (BASF) 0.75% Pd/$\frac{1}{16}$" alumina extrudates E4126E, Evonik Degussa 0.6% Pd/$\frac{1}{16}$" alumina spheres Noblyst 1513, and Johnson Matthey 0.5% Pd on Type 310 trilobe extrudate.

The product stream is withdrawn from the reaction zone. The product stream contains a hydroxy ether reaction product of the cyclic compound(s) with hydrogen. The reaction zone reaction conditions can be set to ensure that the hydroxy ether reaction product remains above its dew point. The reaction conditions can also be set within the reaction zone to ensure that the product stream withdrawn from the reaction zone remains above its dew point and is a vapor. When the product stream is withdrawn from the reaction zone as a vapor, the product stream will also contain other types of compounds in minor amounts, such as by-products, hydrogen gas, and un-reacted cyclic acetal or ketal compounds.

In the vapor phase hydrogenolysis of the cyclic compounds over a heterogeneous supported noble metal catalyst, the noble metal catalyst is not withdrawn in the product stream. The product stream withdrawn advantageously does not contain any appreciable quantities of the noble metal catalyst that have to be separated from the desired hydroxy ether hydrocarbon. In one embodiment of the invention in the product stream withdrawn from the reaction zone contains less than 500 ppmw of the metal catalyst used in the reaction zone, or less than 100 ppmw, or less than 50 ppmw, or less than 25 ppmw, or less than 10 ppmw, or less than 5 ppmw, or less than 2 ppmw, based on the weight of all ingredients fed to the reaction zone.

Suitable hydroxy ether hydrocarbons are the reaction products of the cyclic compounds with hydrogen gas resulting in a hydrocarbon with at least one ether linkage and at least one primary hydroxyl group. The hydroxy ether hydrocarbons may contain secondary hydroxyl groups, and additional ether linkages. In one embodiment, the hydroxy ether hydrocarbons are represented by the general formula:

$R^6OR^7OH$ wherein $R^6$ is a branched or un-branched $C_1$-$C_{50}$ alkyl, $C_2$-$C_{50}$ alkenyl, aryl-$C_1$-$C_{50}$ alkyl, aryl-$C_2$-$C_{50}$ alkenyl-, $C_3$-$C_{12}$ cylcoalkyl, or a $C_3$-$C_{50}$ carboxylate ester; and wherein the alkyl, alkenyl, aryl, and cycloalkyl groups of $R^6$ optionally contain 1, 2, or 3 oxygen atoms in the alkyl, cycloalkyl, or alkenyl group and are optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol.

In the case that the cyclic compound starting material is a cyclic ketal, then $R^6$ branched at least at the carbon adjacent the ether linkage in the general formula above. The branch can be selected from the same groups as $R^6$.

$R^7$ is a branched or un-branched divalent $C_1$-$C_{50}$ alkyl, $C_2$-$C_{50}$ alkenyl, aryl-$C_1$-$C_{50}$ alkyl, aryl-$C_2$-$C_{50}$ alkenyl-, $C_3$-$C_{12}$ cylcoalkyl, or a $C_3$-$C_{50}$ carboxylate ester; and wherein the divalent alkyl, alkenyl, aryl, and cycloalkyl groups of $R^7$ optionally contain 1, 2, or 3 oxygen atoms in the divalent alkyl, cycloalkyl, or alkenyl group and are optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol.

The $R^6$ group of the general formula may be a branched or un-branched $C_1$-$C_{12}$ alkyl or aryl-$C_1$-$C_{12}$ alkyl; optionally substituted with 1, 2, or 3 groups independently selected from —OH, halogen, dialkylamino, aldehyde, ketone, carboxylic acid, ester, ether, alkynyl, dialkylamide, anhydride, carbonate, epoxide, lactone, lactam, phosphine, silyl, thioether, thiol, and phenol.

The $R^7$ group of the general formula may be a divalent branched or un-branched $C_1$-$C_{12}$ alkyl or a $C_2$-$C_{12}$ alkenyl; and wherein the divalent alkyl or alkenyl groups of $R^7$ optionally contain 1, 2, or 3 oxygen atoms in the divalent alkyl or alkenyl groups and are optionally substituted with 1, 2, or 3 groups independently selected from —OH or halogen.

In each case above, the alkyl groups may have from 1-8 carbon atoms, or 1-6 carbon atoms, or 1-4 carbon atoms, and the alkenyl groups may have from 2-8 carbon atoms, or 2-6 carbon atoms, or 2-4 carbon atoms.

Examples of the types of hydroxy ether hydrocarbons that are made by the process of the invention include ethylene glycol propyl ether, ethylene glycol butyl ether, ethylene glycol 2-ethylhexyl ether, diethylene glycol methyl ether, diethylene glycol ethyl ether, diethylene glycol propyl ether, diethylene glycol butyl ether, propylene glycol methyl ether, ether, 3-butoxy-1,2-propanediol, 2-butoxy-1,3-propanediol, 2-isopropoxyethanol, isopropoxy-2-propanol, 3-isopropoxypropanol, 2-(3-methyl-2-butoxy)ethanol, 3-(3-methylbutan-2-yloxy)propanol, 2-(4-methylpentan-2-yloxy)ethanol, 3-(4-methylpentan-2-yloxy)propanol, 3-(4-methylpentan-2-yloxy)-1,2-propanediol, 2-(4-methylpentan-2-yloxy)-1,3-propanediol, 2-(pentan-2-yloxy)ethanol, 3-(pentan-2-yloxy)-propanol, 2-(pentan-2-yloxy)-1,3-propanediol, 3-(pentan-2-yloxy)-1,2-propanediol, 2-(methyl-hexyloxy) ethanol, 3-(methyl-hexyloxy)-propanol, 2-(methyl-hexyloxy)-1,3-propanediol, 3-(methyl-hexyloxy)-1,2-propanediol.

The hydroxy ether hydrocarbons have a wide variety of uses. They can be used as solvents, coalescents and plasticizers in all-purpose cleaners, architectural coatings, automotive coatings, cleaners for ink processes, coalescents for latex paints, coatings for plastics, floor cleaners, solvents for removing photoresists in semiconductor wafers, glass cleaners, household cleaners, industrial cleaners, industrial coatings, and metal brighteners and cleaners. They can be used a solvents for a large variety of coatings resin types, including alkyd, phenolic, maleic, epoxy, and nitrocellulose resins. They are also useful as retarder solvent for lacquers, improving gloss and flow-out. Some of the hydroxy ether hydrocarbons can also be used in amine-solubilized, water-dilutable coatings because of their high flash point, complete water solubility, slow evaporation rate, low surface tension, and high coupling efficiency. As coalescents, they improve film integrity in both architectural and industrial maintenance latex paints.

The desired hydroxy ether hydrocarbon can be readily separated from the product stream. One particularly useful method is to cool the gaseous reactor product stream to below the dew point of the reaction products and unreacted cyclic compounds to form a liquid product and from which a gaseous stream comprised primarily of hydrogen gas (greater than 70 vol. %) is easily separated. When the cooling is carried out at reactor pressure, very little energy is required to re-circulate the un-reacted hydrogen back as a feedstock reactant stream to the reactor vessel. The condensed liquid products may then be recovered and purified by known methods, such as distillation, extraction, crystallization and the like to obtain the desired product. Similarly, a liquid scrubber may be employed to recover condensable liquid products from the gaseous reactor effluent. These and other known methods of product recovery may be used in combination with the hydrogenolysis process of this invention.

The process of the invention is carried out batchwise or continuously, preferably continuously.

Working Examples

The liquid feed part of the hydrogenolysis unit consists of a 100 mm graduated burette feed tank for the acetal feed. This is connected to a flow programmable high pressure lab scale ball and check feed pump (Eldex ReciPro Optos Series Model 1). All equipment under pressure is constructed of 316 stainless steel tubing or fittings. The discharge of the pump leads to ⅛ inch diameter (3.2 mm) tubing that is connected to a fitting on the top of the reactor. This fitting is further connected to a ⅛ inch diameter (3.2 mm) tubing section that leads to a vaporization section prior to the catalyst bed. Hydrogen feed is supplied from high pressure cylinders of zero grade hydrogen via a high pressure regulator to a lab scale Brooks mass flow controller. Nitrogen feed, used for purging and other inert gas needs, is fed by a similar design from a high pressure cylinder via a gas regulator through another dedicated Brooks mass flow controller for inert gas flow. The discharges from these two mass flow controllers are connected by a manifold to a ¼ inch diameter (6.35 mm) tubing feed line that is connected to the top of the reactor. The hydrogen or inert gas feeds enter the reactor by an annulus around the ⅛ inch diameter liquid feed line and mix with the liquid above the vaporization section in the reactor.

The reactor is a 24" (70 cm) long×½" diameter (12.7 mm) section of high pressure tubing held in a vertical arrangement. The top part of the reactor consists of a stainless steel Swagelok cross with the appropriate fittings required to permit liquid feed to the reactor via the ⅛ inch diameter (3.2 mm) tubing, to permit hydrogen or other gas feed to the reactor via ¼ inch (6.35 mm) tubing and to connect to a pressure gage and a safety pressure relief device. The top portion of the reactor consists of a bed 4" (10 cm) deep of fused alumina beads 2-3 mm in diameter that are used for the vaporization of the liquid feed in contact with the gaseous hydrogen feed. A thermocouple is attached to the outside skin of the reactor about 1" (2.54 cm) from the bottom of the vaporization bed and is externally wrapped with heat resistant insulation tape to measure the skin temperature of the metal surface as being heated from the inside by the heated gases. A spacer of Pyrex wool packing is used to separate the vaporizer section from the catalyst section of the bed that is downstream from the vaporizer. The lab unit normally uses 20 cubic centimeters of the hydrogenolysis catalyst used in this invention. The depth of the bed is approximately 10 inches (25 cm) deep. The bed is held in place by another spacer of Pyrex wool packing and a support of ¼ inch (6.35 mm) diameter tubing to hold it in place. A second thermocouple is attached with similar insulation to the outer skin of the reactor tubing about 2 thirds of the depth of the catalyst bed towards the bottom and is used both as a control point and measure of the reactor temperature. The reactor tubing is placed inside a "clam shell" heater that is electrically heated and controlled by the temperature recorded by the thermocouple located near the bottom of the catalyst bed.

The ½ inch (12.7 mm) tubing of the bottom of the reactor is connected by appropriate Swagelok fittings to a 1" 316 stainless steel "T". This "T" is filled with ⅛" stainless steel Penn State packing material as a coalescer and is cooled by way of a circulating bath to copper tubing on the outside of the "T". This "T" is a high pressure vapor/liquid (V/L) separator where liquid product is condensed for recovery. The bottom of the "T" has a needle valve connected to a small section of ⅛" diameter (3.2 mm) tubing where the collected liquid product is drained periodically. The side fitting of the "T" consists of ½ (12.7 mm) tubing that provides an exit for the uncondensed hydrogen and other gases. The side fitting also has a thermocouple in it to measure the inside temperature of the "T". The gases leaving the side tubing of the "T" are then directed upwards to a back pressure regulator that controls the pressure of the reactor. Gases leaving downstream from the back pressure regulator are at ambient pressure and proceed to a dry ice trap to collect any material that may not have been removed in the V/L separator.

Example 1

Vapor Phase Hydrogenolysis Using Degussa 0.5% Pd/Alumina

The liquid feed tank of the unit was filled with a cyclic acetal 2-n-propyl-1,3-dioxolane (PDX). The reactor had been charged with 20 cc (14.27 grams) of Degussa 0.5% Pd/$^1\!/_{16}$" alumina sphere catalyst. The hydrogen flow was set at 2960 sccm and the back pressure regulator was set to 300 psig (2068 kPa). The catalyst bed (skin) temperature target was set at 210 degrees Celsius (483 degrees K.). After reaching 210 degrees (483 degrees K.), the reactor was permitted to equilibrate at 210 degrees Celsius (483 degrees K.) for fifteen minutes. After that period, the PDX pump was started with a target feed rate of 0.12 ml/minute. Liquid product samples were collected hourly as was operating data. The samples were weighed and analyzed by gas chromatographic analysis on Agilent Technologies 6890 series machine having a thermal conductivity detector. The column used was a 30 m J&W 125-3232 DB-FFAP capillary column. A 6 minute hold was used at 40 degrees C. followed by a 10 deg/min heat up rate to a final temperature of 220 deg C. and a final 5 minute hold at 220 deg. C. Response factors were used in normal standard practice to obtain the weights of the different components.

The last four hours of samples and feed level drop were used to perform calculations on the conversion of PDX into the desired product 2-n-butoxyethanol. A total of 26.3 ml of PDX (24.67 grams) was fed during the last four hours. A total of 12.43 grams of PDX was recovered, 11.78 grams of 2-n-butoxyethanol, 0.13 grams of 1,2-n-butoxyethane, 0.05 grams of methyl-n-butylether, 0.19 grams of ethyl n-butyrate, 0.03 grams of ethylene glycol and 0.08 grams of other organic materials were recovered. The conversion of the PDX was 49% with a selectivity of consumed PDX to 2-n-butoxyethanol of 96.4%. The H2/PDX feed mole ratio of this run was 161/1 with the PDX partial pressure in the reactor at 100.4 mm Hg. The specific production rate of the desired 2-n-butoxyethanol was 9.20 lb/cu-ft-hr (147.3 grams/liter-hr).

The Table 1 of runs below used the same charge of catalyst, namely a 20 cc sample of Degussa 0.5% Pd/$^1\!/_{16}$" diameter alumina spheres in the above described unit and demonstrates the effect of better selectivity to desired 2-n-butoxyethanol product with progressively lower partial pressures of PDX in the reactor feed brought about by having higher H2/PDX feed mole ratios.

Example 2

The desired conversion of a cyclic acetal into a hydroxy ether hydrocarbon may be carried out in a vapor phase hydrogenolysis by a wide variety of palladium based catalysts. The highly selective catalysts are those which are not of high activity, that is, those which do not cause extremely high conversions of the cyclic acetal feed across the catalyst bed. Moderate activity catalysts, that is, those that yield a conversion of the cyclic acetal in the 20 to 85 percent range generally yield the best selectivity to the desired hydroxy ether hydrocarbon. Low activity catalysts, yielding conversions of the acetal below 10%, are not as desirable due to the inherent inefficiency of requiring a large amount of acetal recovery for recycle and in most cases also having a poor selectivity to the desired hydroxy ether hydrocarbon product based on converted cyclic acetal. The table below lists the results of several different palladium based catalysts for the conversion of PDX into 2-n-butoxyethanol (EB). All the runs were carried out at a reaction temperature of 200 degrees Celsius (473 degrees K.) with a total reactor pressure of 300 psig (2068 kPa) and a target PDX feed rate of 13.5 grams/hr and a hydrogen feed rate of 700 standard cc/minute. The H$_2$/PDX feed mole ratio was about 18/1. In all examples, 20 cc of catalyst material was packed as a bed in the unit described above. The Table 2 below records the results of runs using different catalysts in terms of grams of product recovered in four hours and a final % selectivity to the desired EB product based on converted PDX.

TABLE 1

| Run Number | T Deg Celsius (K) | Grams PDX/hr | H2/PDX mole ratio | Partial Press PDX mm Hg (kPa) | % PDX Conversion | Grams last 4 hrs EB | Grams last 4 hrs DBE | Grams last 4 hrs MBE | Grams last 4 hrs EtButyr | % Selectivity to EB on converted PDX |
|---|---|---|---|---|---|---|---|---|---|---|
| 2 | 210 (483) | 13.45 | 18.5/1 | 836 (111) | 25 | 9.05 | 0.0 | 0.19 | 1.35 | 83.2 |
| 3 | 210 (483) | 13.45 | 54.4/1 | 294 (39) | 24 | 9.81 | 0.0 | 0.05 | 0.64 | 91.1 |
| 4 | 210 (483) | 13.45 | 92/1 | 175 (23) | 32 | 11.71 | 0.0 | 0.036 | 0.52 | 93.8 |
| 5 | 220 (493) | 13.45 | 91.7/1 | 176 (23) | 44 | 19.00 | 0.14 | 0.072 | 0.72 | 93.6 |
| 6 | 210 (483) | 6.73 | 68.2/1 | 235 (31) | 53 | 11.08 | 0.19 | 0.064 | 0.31 | 94.4 |
| 7 | 210 (483) | 6.73 | 161/1 | 100 (13) | 49 | 11.78 | 0.13 | 0.05 | 0.19 | 96.4 |

*All reactions carried out at 300 psig.
PDX = 2-n-propyl-1,3-dioxolane;
EB = 2-n-butoxyethanol;
MBE = methyl-n-butylether;
EtButyr = ethyl n-butyrate;
DBE = 1,2-di-n-butoxyethane.

TABLE 2

| Run | Catalyst | Milligr. Pd | % Conv. PDX | Gr EB | Gr. DBE | Gr. MBE | Gr. EtButyr | Gr. EG | % Selectivity To EB |
|---|---|---|---|---|---|---|---|---|---|
| 8 | A | 69 | 37 | 17.30 | 0.013 | 0.28 | 1.21 | 0.0 | 91.5 |
| 9 | B | 87 | 45 | 17.23 | 0.027 | 0.29 | 1.17 | 0.22 | 89.5 |
| 10 | C | 45 | 23 | 5.49 | 0.0 | 0.12 | 0.41 | 0.30 | 82.6 |
| 11 | D | 78 | 20 | 9.19 | 0.0 | 0.41 | 1.36 | 0.0 | 82.6 |
| 12 | E | 166 | 6 | 0.76 | 0.0 | 0.03 | 0.29 | 0.0 | 69 |
| 13 | F | 27 | 11 | 2.08 | 0.0 | 0.03 | 0.09 | 0.73 | 57.7 |
| 14 | G | 75 | 94 | 27.26 | 11.23 | 1.00 | 0.80 | 1.89 | 67.1 |
| 15 | H | 135 | 99 | 25.31 | 16.95 | 0.30 | 0.62 | 6.85 | 49.75 |
| 16 | I | 132 | 99 | 24.62 | 16.19 | 0.51 | 0.70 | 6.12 | 50.6 |
| 17 | J | 78 | 80 | 30.07 | 1.00 | 0.45 | 0.13 | 1.39 | 81.2 |
| 18 | K | 175 | 97 | 24.42 | 12.42 | 1.13 | 3.68 | 4.62 | 52.1 |

The catalysts used in the above Table 2 are listed below:
A = Degussa 0.5% Pd/1/16" alumina spheres E exp P/D lot 11DJ022
B = Calsicat (Mallinckrodt Specialty Chemical Co.) 0.5% Pd/1/16" alumina spheres S089-260, E-144SD lot 09D-69A
C = Engelhard (BASF) 0.3% Pd/1/8" alumina spheres
D = Engelhard 1% Pd/1/8" silica "star" extrudates with MgO binder
E = Engelhard 2% Pd/1/8" silica "star" extrudates with MgO binder
F = Sud-Chemie ~0.2% Pd/Ag/1/8" alumina sphere "acetylene case catalyst" G-98B
G = Engelhard (BASF) 0.75% Pd/1/16" alumina extrudates E4126E
H = Engelhard (BASF) 1% Pd/1/16" alumina spheres AS-38
I = Engelhard (BASF) 1% Pd/1/8" alumina spheres AS-38 lot SEO 7473
J = Evonik 0.6% Pd/1/16" alumina spheres Noblyst 1513
K = Evonik 2% Pd/1/16" silicon dioxide extrudates product number 48.7823.4010

As may be seen from the table, the catalysts A-D may be considered as "moderate activity" catalysts and generally gave the highest selectivity to the desired product. Catalysts E and F are low activity catalysts. Catalysts G-K are high activity catalysts, of which catalyst J, having the lowest activity of that subgroup, as measured as % conversion of the acetal, also had the highest selectivity to desired product.

Example 3

The runs in this Example 3 reported below demonstrate that palladium supported on granular carbon support may also be used in this invention without the requirement of having to add ethylene glycol solvent to the feed or to have the requirement of feeding a phosphorus containing acid promoter. The table below records data on the conversion of PDX into 2-n-butoxyethanol, by a bed of 1% Pd/granular carbon catalyst, BASF C 3655 lot SE 08504, 20 cc with a weight of catalyst of 7.83 grams. The carbon supported palladium catalyst generally was not selective to the desired 2-n-butoxyethanol product. The data below in Table 3 lists the average % PDX conversion and % selectivity to desired 2-n-butoxyethanol over the last four hours and the sum of grams of products during the last four hours.

The last run 26 was carried out using nitrogen gas as the feed in lieu of hydrogen gas to demonstrate that the presence of hydrogen is required to prepare significant amounts of desired hydroxy ether hydrocarbon product.

Example 4

Certain modifier additives may be used to modify the performance of the catalysts of this invention. The un-modified Degussa catalyst performed well and to this catalyst modifiers were added. The modifiers were added by the generalized incipient wetness method described below:

Preparation of a Degussa 0.5% Pd/1/16" Alumina Sphere Catalyst Having 0.5 mmole of H3PO4/gram of Catalyst 0.88 grams of 85% aqueous phosphoric acid was added to a 250 milliliter round bottomed flask along with 7.0 ml of de-ionized water. This solution was chilled externally by a water ice bath. 20 cubic centimeters (14.04 grams) of Degussa 0.5% Pd/1/16" alumina sphere catalyst (E exp P/D lot 11DJ022) was added to the flask and swirled rapidly to permit all pellets to absorb the dilute aqueous acid. A vacuum adapter was placed on the round bottomed flask and the cold wet

TABLE 3

| Run | P psig/ kPa | T Celsius/ Kelvin | PDX g/hr | H2 sccm | % PDX Conv. | G EB Last 4 hrs | G DBE Last 4 hrs | G MBE Last 4 hrs | G EtButyr Last 4 hrs | G EG Last 4 hrs | % Selectivity to EB on converted PDX |
|---|---|---|---|---|---|---|---|---|---|---|---|
| 19 | 100/689 | 200/473 | 6.64 | 700 | 75 | 6.03 | 3.58 | 0.89 | 5.34 | 1.43 | 33.8 |
| 20 | 50/345 | 200/473 | 13.3 | 700 | 53 | 6.04 | 2.39 | 0.98 | 9.01 | 1.23 | 29.5 |
| 21 | 50/345 | 170/443 | 13.3 | 700 | 14 | 4.50 | 0.15 | 0.09 | 2.09 | 0.84 | 59.7 |
| 22 | 100/689 | 170/443 | 6.64 | 700 | 44 | 3.97 | 0.92 | 0.09 | 0.92 | 0.77 | 42.1 |
| 23 | 150/1034 | 170/443 | 6.64 | 700 | 54 | 6.80 | 2.16 | 0.07 | 1.02 | 1.27 | 57.6 |
| 24 | 50/345 | 170/443 | 6.64 | 700 | 40 | 4.97 | 1.00 | 0.12 | 1.95 | 0.82 | 53.2 |
| 25 | 150/1034 | 150/423 | 6.64 | 700 | 25 | 4.33 | 0.50 | 0.01 | 0.40 | 0.75 | 64.4 |
| 26 | 50 (N2) 345 kPa | 200/473 | 6.64 | 200 (N2) | 18 | 0.25 | 0.00 | 0.02 | 2.43 | 0.15 | 8.2 | pellets were subjected to 30 mm Hg pressure (4 kPa) by a vacuum pump for about 5 minutes. The pressure was then permitted to return to atmospheric pressure. This vacuum and repressuring was repeated twice more to mix the liquid into all pores of the catalyst. Following this, the pellets were swept with a stream of about 1 liter/minute of dry nitrogen for 48 hours to remove the water and leave behind the non volatile acid. The net weight of final dry catalyst was 14.44 grams.

The Table 4 below shows the effects of additions of different additives to a Degussa 0.5% Pd/¹⁄₁₆" alumina sphere catalyst (E exp P/D lot 11DJ022) on the conversion of PDX into 2-n-butoxyethanol. All runs were carried out at 200 degrees Celsius (473 degrees K.), 300 psig (2068 kPa), with 13.5 grams of PDX fed/hr with a H2/PDX feed mole ratio of about 18/1.

TABLE 4

| Run | Additive | Mmole/g | % PDX Conv. | Gm EB last 4 hr | Gm DBE Last 4 hr | Gm MBE Last 4 hr | Gm EtButyr Last 4 hr | Gm EG Last 4 hr | % Selectivity to EB |
|---|---|---|---|---|---|---|---|---|---|
| 27 | none | 0.0 | 29 | 10.14 | 0.0 | 0.24 | 0.65 | 0.38 | 85.6 |
| 28 | LiOAc | 0.05 | 23 | 6.65 | 0.19 | 0.07 | 0.25 | 0.31 | 86.1 |
| 29 | LiOAc | 0.5 | 9 | 2.44 | 0.0 | 0.14 | 0.57 | 0.0 | 75.9 |
| 30 | H3PO4 | 0.05 | 34 | 13.44 | 0.04 | 0.13 | 0.42 | 0.74 | 86.8 |
| 31 | H3PO4 | 0.5 | 75 | 23.02 | 7.32 | 0.14 | 0.07 | 4.03 | 64.1 |
| 32 | NaH2PO4 | 0.05 | 18 | 6.49 | 0.26 | 0.10 | 0.30 | 0.44 | 81.6 |
| 33 | Ni(OAc)2 | 0.05 | 61 | 18.67 | 2.64 | 0.28 | 0.71 | 1.24 | 78.0 |

The results indicate that the addition of basic materials such as lithium acetate and sodium dihydrogen phosphate retard the rate of reaction. The addition of phosphoric acid increases PDX conversion rate but promotes the formation of DBE above trace (0.05 mmole/gram) amounts. The addition of nickel increased PDX conversion even at trace amounts but significantly increased the formation of the undesired DBE co-product.

Comparison Example 5

The two comparison examples listed below are batch autoclave liquid phase PDX hydrogenolysis runs carried out using pulverized samples of catalysts of this invention. The amount of active metal palladium in each charge was 50 mg. The data below from liquid phase hydrogenolysis reported below does not predict the desirable catalysts to use in the vapor phase hydrogenolysis of this invention.

Batch Autoclave Hydrogenolysis of
2-n-Propyl-1,3-dioxolane (PDX) Using Ethylene
Glycol Co-Solvent with a Pulverized BASF 1%
Pd/carbon granules C 3655 lot SE 08504 Catalyst This same lot of 1% Pd/Carbon catalyst was used to produce the examples listed above. Six grams of BASF 1% Pd/carbon granules C 3655 lot SE 08504 was pulverized in a clean mortar and pestle and sieved to a powder of particles less than 50 mesh. Five grams (5.00 g) of this powder containing a total of 50 mg of palladium was charged to a 300 ml Autoclave Engineers magnetic drive Hastelloy B autoclave. A mixture of 20.0 grams of PDX and 100.0 grams of ethylene glycol co-solvent was prepared in a 250 ml beaker and mixed thoroughly and added to the autoclave base containing the pulverized palladium/carbon catalyst. The contents of the autoclave were mixed by stirring with a spatula. The autoclave head was placed on the base and the head bolts torqued to secure the autoclave base. The autoclave was then purged with nitrogen to displace any air. The autoclave was then pressured to 400 psig (2758 kPa) with hydrogen and the magnetic stirrer started. The autoclave was heated to 200 degrees Celsius (473 degrees K.) and the pressure adjusted to 500 psig (3447 kPa). The reaction was permitted to run for 1 hour. Following this, the autoclave was cooled to ambient temperature and vented of its pressure. The contents of the autoclave were removed and the solid catalyst was removed from the liquid by filtration. The liquid product was then analyzed by normal gas chromatographic methods described previously. The liquid product contained: PDX 3.41 grams; 2-n-butoxyethanol 10.78 grams; 1,2-di-n-butoxyethane 0.30 grams; ethylene glycol 99.65 grams, grams, to obtain a % conversion of 82.9% and a selectivity of 97.3% to the EB product.

Batch Autoclave Hydrogenolysis of
2-n-Propyl-1,3-dioxolane (PDX) Using Ethylene
Glycol Co-solvent With a Pulverized Degussa 0.5%
Pd/Alumina E exp P/D lot 11 DJ022 Catalyst A sample (12 grams) of Degussa 0.5% Pd/¹⁄₁₆" Alumina sphere catalyst E exp P/D lot 11 DJ022 was pulverized in a clean mortar and pestle to below 120 mesh powder. Ten (10.0) grams of this powdered catalyst containing 50 mg of palladium was added to the base of a 300 ml Autoclave Engineers magnetic drive Hastelloy B autoclave. A mixture of PDX (20.0 grams) and ethylene glycol (100.0 grams) co-solvent were prepared in a 250 ml beaker and mixed well and then added to the base of the autoclave. The contents in the autoclave were stirred with a spatula prior to placing the autoclave head on the base. After applying torque to the head bolts to secure the autoclave, it was purged with nitrogen to displace any air. The autoclave was pressured to 400 psig (2758 kPa) with hydrogen and heated with stirring to 200 degrees Celsius (473 degrees K.). At 200 degrees C. (473 degrees K.), the pressure was adjusted to 500 psig (3447 kPa) and the reaction was run for one hour. After the one hour period, the autoclave was cooled to ambient temperature and the pressure vented. The contents were removed and filtered. The filtration was difficult. A total of 88.4 grams of liquid product was recovered. The amount of compounds contained in this material was: PDX 6.0 grams, water 1.0 grams, ethylene glycol 81.4 grams, no 2-n-butoxyethanol product was observed to obtain a % conversion of 59.5% and a selectivity of 0% to the EB product.

What we claim is:
1. A hydrogenolysis process comprising:
(a) feeding hydrogen and a cyclic compound composition to a reaction zone within a reaction vessel, said cyclic compound composition comprising cyclic acetal compounds having two oxygen atoms single bonded to the same carbon atom in the ring structure, cyclic ketal compounds having two oxygen atoms single bonded to the same carbon atom in the ring structure, or a combination thereof, and (b) conducting a reaction in the reaction zone comprising contacting the hydrogen with at least a portion of the cyclic compound composition in the vapor phase in the reaction zone under reaction zone conditions above the dew point of the cyclic compound composition to produce hydroxy ether hydrocarbons having at least one ether linkage and at least one primary hydroxyl group, and (c) withdrawing a product stream from the reaction zone comprising the hydroxy ether hydrocarbons, hydrogen, and if present any unreacted cyclic compounds;

wherein the selectivity to the hydroxy ether hydrocarbons is greater than 80 mole %.

2. The process of claim 1, wherein the cyclic compound composition is a vapor prior to entry into the reaction zone.

3. The process of claim 1, wherein the reaction zone conditions are above the dew point of product stream.

4. The process of claim 1, wherein the cyclic compound composition comprises a cyclic ketal.

5. The process of any one of claim 2 or 3, wherein the product stream withdrawn from the reaction zone is a vapor.

6. The process of claim 1, wherein a feed of hydrogen and a feed of cyclic compound composition are in combination within a pipe prior to entry into the reaction zone.

7. The process of claim 1, wherein the reaction in the reaction zone is conducted in the absence of a liquid compound.

8. The process of claim 1, wherein the cyclic compound composition comprises a cyclic acetal.

9. The process of claim 8, wherein the cyclic acetal comprises the reaction product of a polyhydroxyl compound and an aldehyde.

10. The process of claim 9, wherein the polyhydroxyl compound comprises ethylene glycol, 1,2-propanediol, 1,3-propanediol, 1,4-butanediol, 1,3-butanediol, diethylene glycol, triethylene glycol, or combinations thereof.

11. The process of claim 9, wherein the aldehyde compound comprises acetaldehyde, propionaldehyde, butyraldehyde, isobutyraldehyde, pentaldehyde, 2-methylbutyraldehyde, 3-methylbutyraldehyde, hexaldehyde, benzaldehyde, 2-ethylhexaldehyde, 1,3-cyclohexanedicarboxaldehyde, 1,4-cyclohexanedicarboxaldehyde, or combinations thereof.

12. The process of claim 8, wherein the cyclic acetal comprises 2-propyl-1,3-dioxolane.

13. The process of claim 1, wherein the temperature of the reaction zone is at least 150° C.

14. The process of claim 13, wherein the temperature of the reaction zone is at least 180° C.

15. The process of any one of claims 13 through 14, wherein the partial pressure within the reaction zone is above the dew point of all the cyclic compounds within the composition fed to the reaction zone at reaction zone temperature.

16. The process of any one of claims 13-14, wherein the pressure within the reaction zone ranges from 13 to 141 atmospheres standard.

17. The process of any one of claims 13-14, wherein the pressure within the reaction zone ranges from 20 to 88 atmospheres standard.

18. The process of claim 1, wherein the selectivity to the hydroxy ether hydrocarbons is at least 90 mole %.

19. The process of claim 18, wherein the selectivity to the hydroxy ether hydrocarbons is at least 95 mole %.

20. The process of any one of claims 18-19, wherein the conversion of the cyclic compound composition is at least 40 mole %.

21. The process of any one of claims 18-19, wherein the conversion of the cyclic compound composition is at least 50 mole %.

22. The process of claim 1, comprising (a) feeding hydrogen gas and 1,3-cyclic acetal compounds to a reaction zone within a reaction vessel, and (b) contacting the hydrogen with at least a portion of the cyclic compound composition in the reaction zone at a pressure of at least 100 psig and at a temperature that satisfies all the following conditions:
(i) is at least 150° C., and
(ii) is above the dew point of the cyclic compound composition at the pressure within the reaction zone,
(iii) is above the dew point of the product stream at the pressure within the reaction zone, and wherein there is no liquid present in the reaction zone during the reaction, and (c) withdrawing a product stream from the reaction zone comprising hydroxy ether hydrocarbons having at least one ether linkage and at least one primary hydroxyl group, hydrogen, and if present any unreacted cyclic compounds, and (d) separating hydrogen from the product stream to form a hydrogen stream and a separated product stream.

23. The process of claim 22, wherein hydrogen is separated from the product stream by condensing to a liquid the hydroxy ether hydrocarbons, hydrogen, and if present any unreacted cyclic compounds in the product stream and separating hydrogen gas from the liquid.

24. The process of claim 23, wherein the 1,3-cyclic acetal compound contains a 1,3-dioxolane moiety.

25. The process of claim 24, wherein the 1,3-cyclic acetal compound comprises 2-propyl-1,3-dioxolane.

26. The process of claim 1, wherein the process is conducted in the presence of a noble metal catalyst comprising palladium.

27. The process of claim 26, wherein palladium catalyst is supported on an aluminum oxide support or a zirconium oxide support.

28. The process of claim 27, wherein the weight % dispersion of palladium on the support is no more than 5 wt %, and the surface area of the aluminum oxide or zirconium oxide support is no more than 300 m$^2$/g.

29. A hydrogenolysis process comprising reacting cyclic compounds having two oxygen atoms single bonded to the same carbon atom in the ring structure with hydrogen in a reaction zone over a noble metal catalyst in the absence of a liquid in the reaction zone to produce hydroxyl ether hydrocarbons having at least one ether linkage and at least one primary hydroxyl group, wherein said cyclic compounds comprise cyclic acetals, cyclic ketals, or a combination thereof, wherein the selectivity to said hydroxy ether hydrocarbons is greater than 80 mole %.

30. The process of claim 29, wherein the cyclic compounds comprise cyclic acetal compounds, said cyclic acetal compounds comprising the reaction product of:

(i) ethylene glycol, 1,2-propanediol, 1,3-propanediol, 1,4-butanediol, 1,3-butanediol, diethylene glycol, triethylene glycol, or combinations thereof, with (ii) acetaldehyde, propionaldehyde, butyraldehyde, isobutyraldehyde, pentaldehyde, 2-methylbutyraldehyde, 3-methylbutyraldehyde, hexaldehyde, benzaldehyde, 2-ethylhexaldehyde, 1,3-cyclohexanedicarboxaldehyde, 1,4-cyclohexanedicarboxaldehyde, or combinations thereof.

31. The process of claim 30, wherein the cyclic acetal comprises 2-propyl-1,3-dioxolane.

32. The process of claim 29, wherein the hydroxy ether hydrocarbons comprises 2-n-butyoxyethanol.

33. The process of any one of claims 29-32, wherein the reaction in the reaction zone is conducted in the absence of ethylene glycol.

34. A process comprising contacting cyclic compounds containing 1,3-dioxolane moeities in the vapor phase with hydrogen in a reaction zone to produce a vapor hydroxy ether hydrocarbon, wherein said cyclic compounds are fed to the reaction zone as a vapor, and wherein the selectity of the process to the production of hydroxy ether hydrocarbons is at least 80%.

35. The process of claim 34, comprising withdrawing from the reaction zone a vapor product stream comprising vapor hydroxy ether hydrocarbons.

36. The process of claim 35, wherein the selectivity of the process to the production of hydroxy ether hydrocarbons is at least 90%.

37. The process of any one of claims 34-36, wherein the cyclic compounds comprise cyclic acetal compounds.

38. A hydrogenolysis process comprising feeding hydrogen and cyclic compounds, comprising cyclic acetal compounds having two oxygen atoms single bonded to the same carbon atom in the ring structure, cyclic ketal compounds having two oxygen atoms single bonded to the same carbon atom in the ring structure, or a combination thereof, to a reaction zone and reacting hydrogen and the cyclic compounds, in the vapor phase, in the presence of a -catalyst composition and withdrawing from the reaction zone a product stream comprising hydroxy ether hydrocarbons having at least one ether linkage and at least one primary hydroxyl group, wherein said catalyst composition comprises:

A. palladium on an aluminum oxide support or a zirconium oxide support at a loading ranging from more than 0.2 wt. % up to 1 wt. % based on the weight of the catalyst composition, said support having a BET surface area of less than 300 $m^2$/g, or B. palladium metal supported on an aluminum oxide support or a zirconium oxide support at a loading ranging from 0.1 wt. % up to 2 wt. %, said support doped with an alkali metal composition comprising C1-C8 carboxylates and halides of Li, other than lithium acetate, K, Na, Rb, Cs, or an alkaline earth metal; or a triphosphine oxide compound.

39. The process of claim 38, wherein the product stream contains less than 50 ppmw noble metal catalyst.

40. The process of claim 39, wherein the product stream contains less than 10 ppmw noble metal catalyst.

41. The process of any one of claims 38-40, wherein the cyclic compounds comprise cyclic acetal compounds, the process is continuous, and the noble metal catalyst is palladium.

42. The process of claim 38, wherein the product stream withdrawn from the reaction zone is a vapor.

43. The process of claim 42, wherein the cyclic compounds fed to the reaction zone are a vapor.

44. The process of claim 38, wherein the catalyst support composition comprises catalyst composition A, comprising:
an α-aluminum oxide support having a BET surface area of less than 30 m2/g, or
(ii) a γ-aluminum oxide support having a BET surface area of less than 300 m2/g, or
(iii) a zirconium oxide support having a BET surface area of up to 100 m2/g.

45. The process of claim 38, wherein the support contains less than 0.5 wt % silicon dioxide.

46. The process of claim 38, wherein the catalyst composition comprises catalyst B.

47. The process of claim 46, wherein the support is doped with potassium acetate, barium acetate, potassium fluoride, or sodium fluoride.

48. The process of claim 38, wherein the palladium loading is up to 0.6 wt. %.

\* \* \* \* \*